(12) United States Patent
Harrer et al.

(10) Patent No.: US 10,370,427 B2
(45) Date of Patent: Aug. 6, 2019

(54) INFLUENZA-SPECIFIC T-CELL RECEPTOR AND ITS USES IN THE DETECTION, PREVENTION AND/OR TREATMENT OF INFLUENZA

(71) Applicant: Friedrich-Alexander Universität Erlangen-Nürnberg, Erlangen (DE)

(72) Inventors: Thomas Harrer, Erlangen (DE); Angela Hückelhoven, Berglen (DE)

(73) Assignee: Friedrich-Alexander Universität Erlangen-Nürnberg, Erlanen (DE)

( * ) Notice: Subject to any disclaimer, the term of this patent is extended or adjusted under 35 U.S.C. 154(b) by 288 days.

(21) Appl. No.: 15/106,292

(22) PCT Filed: Dec. 18, 2014

(86) PCT No.: PCT/EP2014/078502
§ 371 (c)(1),
(2) Date: Jun. 18, 2016

(87) PCT Pub. No.: WO2015/091823
PCT Pub. Date: Jun. 25, 2015

(65) Prior Publication Data
US 2016/0297864 A1    Oct. 13, 2016

(30) Foreign Application Priority Data
Dec. 19, 2013    (EP) ..................................... 13198519

(51) Int. Cl.
*A61K 38/00* (2006.01)
*C07K 14/725* (2006.01)
*G01N 33/569* (2006.01)

(52) U.S. Cl.
CPC ... *C07K 14/7051* (2013.01); *G01N 33/56983* (2013.01); *A61K 38/00* (2013.01); *C07K 2319/70* (2013.01); *G01N 2333/11* (2013.01)

(58) Field of Classification Search
None
See application file for complete search history.

(56) References Cited

FOREIGN PATENT DOCUMENTS

| WO | WO 99/60120 A2 | 11/1999 |
|----|----------------|---------|
| WO | WO 2007/131092 A2 | 11/2007 |
| WO | WO 2008/039818 A2 | 4/2008 |
| WO | WO 2012/038055 A1 | 3/2012 |

OTHER PUBLICATIONS

GenBank Accession # CAA06180, TCR alpha chain [*Homo sapiens*], 1998.*
Berdien, Belinda et al., "Influenza virus-specific TCR-transduced T cells as a model for adoptive immunotherapy," *Human Vaccines & Immunotherapeutics*, Jun. 2013, 9(6):1205-1216.
DataBase EMBL, Mar. 10, 2001, "*Homo sapiens* partial BV22S1J1.1 gene for T-cell receptor beta chain VJ region, patient A4, 237 BP," retrieved from EBI accession No. EM_STD:AJ301443, XP002721410.
Lehner, Paul J. et al., "Human HLA-A0201-restricted Cytotoxic T Lymphocyte Recognition of Influenza A is Dominated by T Cells Bearing the Vβ17 Gene Segment," *The Journal of Experimental Medicine*, Jan. 1, 1995, 181(1):79-91.
Liu, Jun et al., "Conserved epitopes dominate cross-CD8$_+$T-cell responses against influenza A H1N1 virus among Asian populations," *European Journal of Immunology*, Jun. 14, 2013, 43(8):2055-2069.

* cited by examiner

*Primary Examiner* — Benjamin P Blumel
(74) *Attorney, Agent, or Firm* — Saliwanchik, Lloyd & Eisenschenk

(57) ABSTRACT

The present invention relates to specific T-cell receptor a-chains, T-cell receptor β-chains and T-cell receptors comprising said T-cell receptor a-chain and/or β-chain. In particular, the invention relates to T-cell receptors and/or chains binding to the influenza matrix peptide GILGFVFTL (GL9 peptide) presented by Human Leukocyte antigen A2 (HLA-A2) molecules. The present invention further relates to soluble TCR constructs, chimeric TCRs, nucleic acids, expression constructs and cells comprising said TCR a-chain and/or β-chain or the respective TCR. The present invention further relates to the use of the TCR a-chain and/or β-chain or the respective TCR or the soluble TCR constructs or chimeric TCRs as a medicament, preferably in the detection, prevention and/or treatment of influenza. The present invention further relates to methods of detecting, preventing and/or treating influenza.

Figure 1:
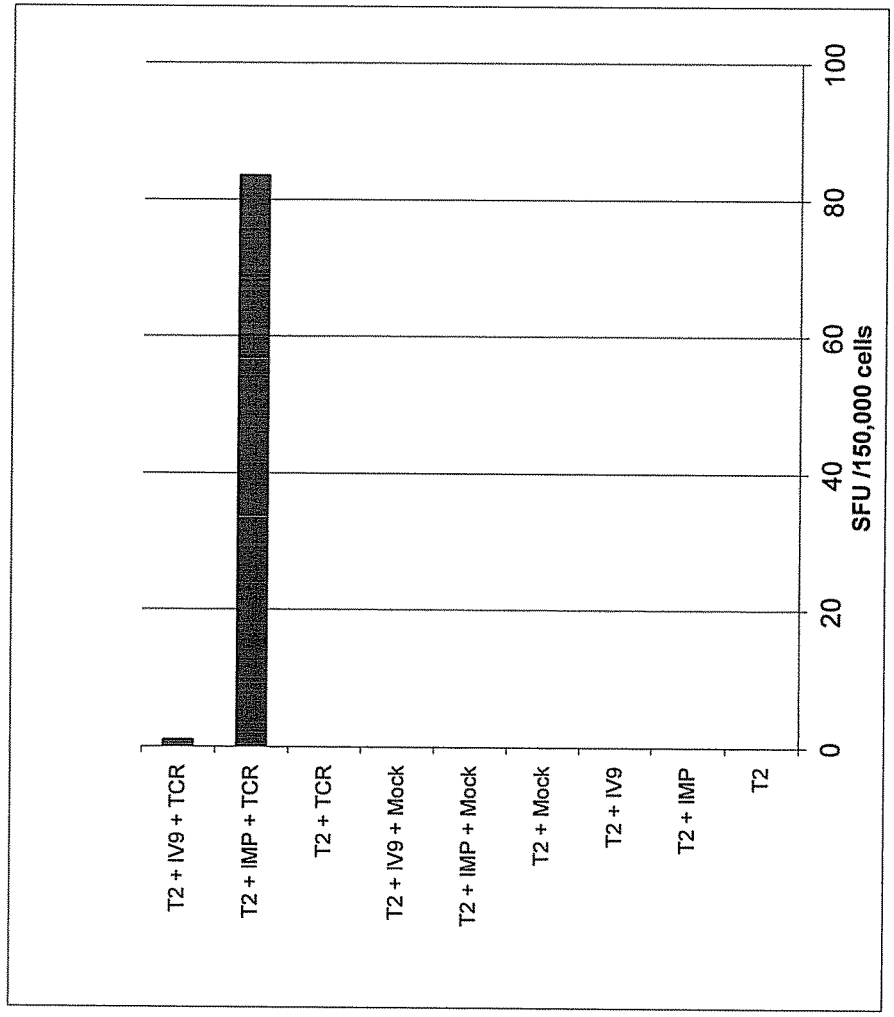
Figure 2:
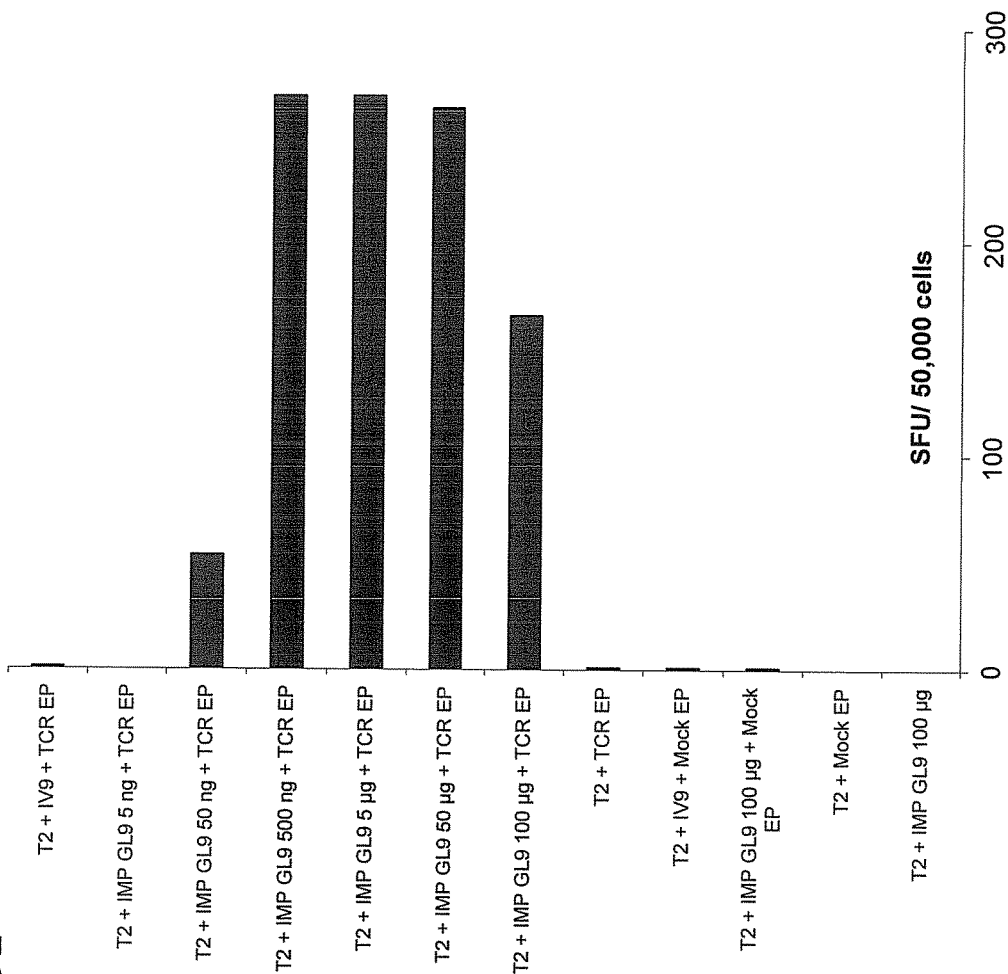

11 Claims, 4 Drawing Sheets
Specification includes a Sequence Listing.

Figure 3

Nucleotide sequence TCR alpha chain

ATGGCCTCTGCACCCATCTCGATGCTTGCGATGCTCTTCACATTGAGTGGGCTGAGAGCTCAGTCAGTGGCT
CAGCCCGGAAGATCAGGTCAACGTTGCTGAAGGGAATCCCTGACTGTGAAATGCACCTATTCAGTCTCTGGA
AACCCTTATCTTTTTTGGTATGTTCAATACCCCAACGAGGCCTCCAGTTCCTTCTGAAATACATCACAGGG
GATAACCTGGTTAAAGGCAGCTATGGCTTTGAAGCTGAATTTAACAGAGCCAAACCTCCTTCCACCTGAAG
AAACCATCGCTGTGAGCGACTCCGCTTTGTACTTCTGTGCTGTGAGAGATC<u>TTAACACCAATGCAGGC</u>
<u>AAATCAACCTTTGGGGATGGGACTACGCTGCTCACTGTGAAGCCAA</u>ATATCCAGAACCCTGACCCTGCCGTGTAC
CAGCTGAGAGACTCTAAATCCAGTGACAAGTCTGTCTGCCTATTCACCGATTTTGATTCTCAAACAAATGTG
TCACAAAGTAAGGATTCTGATGTGTATATCACAGACAAATCTGACTTTGCATGTGCAAACGCCTTCAACAACAGCATTATT
AGCAACAGTGCTGTGTGGAGCAACAAATCTGACTTTGCATGTGCAAACGCCTTCAACAACAGCATTATT
CCAGAGACACCTTCTTCCCCAGCCAGCTCCTGTGATGTCAAAGTTCCTGTGATGTCAGTTCCCGAATCCCTCTCCCTGAAAGTGGCCGGGTTT
GATACGAACCTAAACTTTCAAAACTTGTCAGTGATTGGGTTCCGAATCCCTCTCCCTGAAAGTGGCCGGGTTT
AATCTGCTCATGACGCTGCGCGGCTGTGGTCCAGC

Amino acid sequence

MASAPISMLAMLFTLSGLRAQSVAQPEDQVNVAEGNPLTVKCTYSVSGNPYLFWYVQYPNRGLQFLLKYITG
DNLVKGSYGFEAEFNKSQTSFHLKKPSALVSDSALYFCAVRD<u>LNTNAGKSTFGDGTTLTVKP</u>NIQNPDPAVY
QLRDSKSSDKSVCLFTDFDSQTNVSQSKDSDVYITDKTVLDMRSMDFKSNSAVAWSNKSDFACANAFNNSII
PEDTFFPSPESSCDVKLVEKSFETDTNLNFQNLSVIGFRILLLKVAGFNLLMTLRLWSS

Figure 4

Nucleotide sequence TCR beta chain

ATGAGCAACCAGGTGCTCTGCTGTGTGGTCCTTGTTCCTGGAGCAAACACCGTGGATGGTGGAATCACT
CAGTCCCCAAAGTACCTGTTCAGAAAGGAAGGACAGAATGTGACCCTGAGTTGTGAACAGAATTTGAACCAC
GATGCCATGTACTGGTACCGACAGGACCCAGGGCAAGGCTGAGATTGATCTACTACTCACAGATAGTAAAT
GACTTTCAGAAAGGAGATATAGCTGAAGGGTACAGCGTCTCTCGGGAGAAGAAGAATCCTTTCCTCTACT
GTGACATCGGCCCAAAAGAACCGACAGCTTTCTATCTCTGTGCCAGTAGTTCTACAATCGGGCACTGAAGCT
TTCTTTGGACAAGGCACCAGACTCACAGTTGTAGAGGACCTGAACAAGGTGTTCCCACCCGAGGTCGCTGTG
TTTGAGCCATCATCAGAAGCAGAGATCTCCCACACCCAAAAGGCCACACTGGTGTGCCTGGCCACAGAGACCCGCAG
CCTGACCACGTGGAGCTGAGCTGGTGGGTGAATGGGAAGGAGGTGCACAGTGACCCGCCTGAGCCGCCACC
CCCCTCAAGGAGGAGCAGCCCCGCCAACCACTTCCGCTGTCAAGTCCAGTTCTACGGGCTCTCGGAGAATGACGAGTGG
TTCTGGCAGAACCCCGCCAACCACTTCCGCTGTCAAGTCCAGTTCTACGGGCTCTCGGAGAATGACGAGTGG
ACCCAGGATAGGGCCAAAACCCGTCACCCAGATCGTCAGCGCCCAGCCTCTGGGGTAGAGCAGAGACTGGCTTT
ACCTCGGTGTCCTACCAGCAAGGGGTCCTCTGCCACCATCCTCTATGAGATCCTGCTAGGGAAGGCCACC
CTGTATGCTGTGCTGGTCAGCGCCCTTGTGTTGATGGCCATGGTCAAGAGAAAGGATTTC

Amino acid sequence

MSNQVLCCVVLCFLGANTVDGGITQSPKYLFRKEGQNVTLSCEQNLNHDAMYWYRQDPGQGLRLIYYSQIVN
DFQKGDIAEGYSVSREKKESFPLTVTSAQKNPTAFYLCASSSSTSGTEAFFGQGTRLTVVEDLNKVFPPEVAV
FEPSEAEISHTQKATLVCLATGFFPDHVELSWWVNGKEVHSGVSTDPQPLKEQPALNDSRYCLSSRLRVSAT
FWQNPRNHFRCQVQFYGLSENDEWTQDRAKPVTQIVSAEAWGRADCGFTSVSYQQGVLSATILYEILLGKAT
LYAVLVSALVLMAMVKRKDF

INFLUENZA-SPECIFIC T-CELL RECEPTOR AND ITS USES IN THE DETECTION, PREVENTION AND/OR TREATMENT OF INFLUENZA

CROSS REFERENCE TO RELATED APPLICATIONS

This application is a National Stage Application of International Application Number PCT/EP2014/078502, filed Dec. 18, 2014; which claims priority to European Application No. 13198519.4, filed Dec. 19, 2013; which are incorporated herein by reference in their entirety.

The Sequence Listing for this application is labeled "SeqList-02Jun16.txt", which was created on Jun. 2, 2016, and is 12 KB. The entire content is incorporated herein by reference in its entirety.

The present invention relates to specific T-cell receptor α-chains, T-cell receptor β-chains and T-cell receptors comprising said T-cell receptor α-chain and/or β-chain. In particular, the invention relates to T-cell receptors and/or chains binding to the influenza matrix peptide GILGFVFTL (GL9 peptide) presented by Human Leukocyte antigen A2 (HLA-A2) molecules. The present invention further relates to soluble TCR constructs, chimeric TCRs, nucleic acids, expression constructs and cells comprising said TCR α-chain and/or β-chain or the respective TCR. The present invention further relates to the use of the TCR α-chain and/or β-chain or the respective TCR or the soluble TCR constructs or chimeric TCRs as a medicament, preferably in the detection, prevention and/or treatment of influenza. The present invention further relates to methods of detecting, preventing and/or treating influenza.

BACKGROUND OF THE INVENTION

Influenza, commonly known as "the flu", is an infectious disease of birds and mammals caused by RNA viruses of the family Orthomyxoviridae, the influenza viruses.

Influenza viruses lead to perilous infections in humans. Aside of the known human influenza viruses there are numerous influenza viruses in animals with the potential to infect humans such as swine flu viruses or avian flu viruses. The immune system can prevent the infection by the generation of neutralizing antibodies, however due to their high mutation rate and high variability in their surface hemagglutinin molecules influenza viruses can escape from the recognition by antibodies. Mutations in viral genes and reassorting of viral genes in infected cells are the major driving forces for the development of new influenza epidemics.

Aside of antibodies, cytotoxic T-cells (CTL) play an important role in the control of influenza viruses. Although they cannot prevent the infection of a cell, they are crucial to the control of infection by the elimination of virus infected cells. Influenza-specific CD8+ T-cells recognize by their T-cell receptor usually 8 to 10 amino acid long peptides which are generated from viral proteins by cellular proteasomes within the cytoplasm of infected cells. After binding to HLA class I-molecules, the peptide/HLA-complexes are transported to the cell surface for presentation to CD8+ cytotoxic T-cells (CTL). The binding of the specific T-cell receptor of the CTL with the HLA-I/peptide-complex, leads to activation of the CTL with subsequent lysis of the infected cell by the CTL.

The T-cell receptor of the HLA-class I-restricted CD8+ CTL consists of two proteins, the TCR alpha chain and the TCR-beta-chain. Both the TCR-alpha-chain and the TCR-beta-chain are formed from various gene segments, which are rearranged from a variety of variable gene segments at the TCR-alpha locus and the TCR-beta locus. The TCR-alpha chain consists of a variable (V) gene segment, a J (Joining) gene segment and a constant (C) gene segment. The TCR-beta chain consists of a variable (V) gene segment, a J (Joining) gene segment, a D (diversity) gene segment and a constant (C) gene segment.

The individual TCR of individual T-cells is generated during the thymocyte development by recombination of gene segments. D-to-J recombination occurs first in the β chain of the TCR. This process can involve either the joining of the Dβ1 gene segment to one of six Jβ1 segments or the joining of the Dβ2 gene segment to one of seven Jβ2 segments. DJ recombination is followed (as above) with Vβ-to-DβJβ rearrangements. All gene segments between the Vβ-Dβ-Jβ gene segments in the newly forming complex are deleted and the primary transcript is synthesized that incorporates the constant domain gene (Vβ-Dβ-Jβ-Cβ). mRNA transcription splices out any intervening sequence and allows translation of the full length protein for the TCR Cβ chain.

The rearrangement of the alpha (α) chain of the TCR follows β chain rearrangement, and resembles V-to-J rearrangement described for Ig light chains (see above). The diversity of the somatically rearranged TCRs is enhanced further by the introduction of additional nucleotides between the V and J gene segments of rearranged TCR-alpha genes. The rearrangement of TCR gene segments provide a diverse repertoire of approximately $10^{18}$ different TCRs. The TCR-alpha-chain and the TCR-beta-chain pair after their synthesis to yield the αβ-TCR-heterodimer that is expressed on a majority of T cells.

The specificity of the recognition of the viral peptides is mainly determined by the CDR3-region of both the TCR-alpha and the TCR-beta chains. Each CTL usually expresses only a single functional T-cell receptor (TCR) that allows the recognition of only a single antigenic peptide. Dependent on the individual TCR sequence, TCRs can exhibit a certain cross-reactivity that may allow also the recognition of peptide variants to a certain degree.

In the prior art influenza-specific T-cell receptors (TCR) are known (Berdien et al., 2013). Verna et al. (2004) describe tumor growth inhibition by hTER-transduced T cells. Thereby, they describe CTLs which specifically recognize the influenza matrix protein 58-66 (GILGFVFTL) on HLA-A2-positive cells.

Viral matrix proteins are structural proteins linking the viral envelope with the virus core. They play a crucial role in virus assembly, and interact with the RNP complex as well as with the viral membrane. They are found in Morbillivirus, Paramyxovirus, Orthomyxovirus and Pneumovirus. The M1 protein of the influenza virus is a viral matrix protein, showing affinity to the glycoproteins inserted in the host cell membrane on one side and affinity for the RNP complex molecules on the other side, which allows formation at the membrane of a complex made of the viral ribonucleoprotein at the inner side indirectly connected to the viral glycoproteins protruding from the membrane. This assembly complex will now bud out of the cell as new mature viruses. Viral matrix proteins, like many other viral proteins may exert different functions during the course of the infection.

US 2006/0155115 A1 describes synthetic multivalent T-cell receptor complexes for binding to a MHC-peptide complex, which multivalent TCR complex comprises a plurality of TCRs specific for the MHC-peptide complex. The TCRs are refolded recombinant soluble TCRs. One of the TCRs described is specific for the epitope$_{58-66}$ of the influenza matrix protein in HLA-A2.

WO 2012/038055 A1 describes tumor antigen-specific TCRs and T-cell epitopes. The TCRs which are directed against the human tumor antigen TPTE were cloned from CD4+ T cells, which recognize peptides with HLA-2.

WO 2008/039818 A2 describes a modified TCR. WO 2007/131092 A2 discloses chimeric TCRs which are tumor-specific.

There is a need in the art for improved means and methods for detecting, preventing and/or treating influenza, in particular via influenza-antigen specific cells or by immunotherapy.

SUMMARY OF THE INVENTION

According to the present invention this object is solved by a T-cell receptor α-chain or a T-cell receptor comprising said T-cell receptor α-chain, wherein said T-cell receptor α-chain comprises the amino acid sequence of SEQ ID NO. 1 or an amino acid sequence that has at least 80% identity to the amino acid sequence of SEQ ID NO. 1, or any variation of the TCR sequence provided that this variation retains its functional ability to bind to the GL9/HLA-A2-complex.

According to the present invention this object is solved by a T-cell receptor β-chain or a T-cell receptor comprising said T-cell receptor β-chain, wherein said T-cell receptor β-chain comprises the amino acid sequence of SEQ ID NO. 3 or an amino acid sequence that has at least 77% identity to the amino acid sequence of SEQ ID NO. 3, or any variation of the TCR sequence provided that this variation retains its functional ability to bind to the GL9/HLA-A2-complex.

According to the present invention this object is solved by a T-cell receptor comprising:
  (i) a T cell receptor α-chain comprising the amino acid sequence of SEQ ID NO. 1 or SEQ ID NO. 2, or an amino acid sequence that has at least 80% identity to the amino acid sequence of SEQ ID NO. 1 or an amino acid sequence that has at least 85% identity to the amino acid sequence of SEQ ID NO. 2, or any variation of the TCR sequence provided that this variation retains its functional ability to bind to the GL9/HLA-A2-complex, and
  (ii) a T-cell receptor β-chain comprising the amino acid sequence of SEQ ID NO. 3 or SEQ ID NO. 4, or an amino acid sequence that has at least 77% identity to the amino acid sequence of SEQ ID NO. 3 or an amino acid sequence that has at least 85% identity to the amino acid sequence of SEQ ID NO. 4, or any variation of the TCR sequence provided that this variation retains its functional ability to bind to the GL9/HLA-A2-complex.

According to the present invention this object is solved by a soluble T-cell receptor (sTCR) construct comprising
(1) at least one of the T-cell receptor α-chain(s) of the present invention and/or the T-cell receptor β-chain(s) of the present invention,
  preferably covalently linked to each other to form TCR heterodimers or multimers, and (2) fusion component(s)
  preferably selected from Fc receptors and/or Fc domains, cytokines, such as IL-2 or IL-15, toxins, such as exotoxin A, Pseudomonas exotoxin, antibodies, such as anti-CD3-antibodies, or combinations thereof,
wherein the at least one T-cell receptor chain (1) is bound to the fusion component(s) (2).

According to the present invention this object is solved by a chimeric T-cell receptor comprising at least one of
  the T-cell receptor α-chain of the present invention,
  the T-cell receptor β-chain of the present invention, or
  the T-cell receptor of the present invention,
wherein the TCR α-chain and/or the TCR β-chain is/are fused to CD3-zeta chain(s).

According to the present invention this object is solved by a nucleic acid encoding the T-cell receptor chain or T-cell receptor according to the present invention or encoding the soluble T-cell receptor construct according to the present invention or encoding the chimeric T-cell receptor according to the present invention.

According to the present invention this object is solved by an expression construct for expressing the T-cell receptor chain or T-cell receptor or soluble T-cell receptor construct or chimeric T-cell receptor according to the present invention in a cell.

According to the present invention this object is solved by a cell comprising the T-cell receptor chain or T-cell receptor or soluble T-cell receptor construct or chimeric T-cell receptor according to the present invention or the nucleic acid(s) of the present invention or the expression construct of the present invention.

According to the present invention this object is solved by a pharmaceutical composition comprising one or more of:
  (i) the T-cell receptor α-chain of the present invention;
  (ii) the T-cell receptor β-chain of the present invention;
  (iii) the T-cell receptor of the present invention;
  (iv) the soluble T-cell receptor construct of the present invention;
  (v) the chimeric T-cell receptor of the present invention;
  (vi) the nucleic acid(s) of the present invention or the expression construct of the present invention; and/or
  (vii) the cell of the present invention,
and, optionally, pharmaceutically excipient(s).

According to the present invention this object is solved by the use of a T-cell receptor chain or T-cell receptor of the present invention, a chimeric T-cell receptor of the present invention, a nucleic acid of the present invention or an expression construct of the present invention for generating genetically modified lymphocytes.

According to the present invention this object is solved by providing the T-cell receptor chain or T-cell receptor of the present invention, the soluble T-cell receptor construct of the present invention, the chimeric T-cell receptor of the present invention, the nucleic acid of the present invention, the expression construct of the present invention or the host cell of the present invention for use as a medicament.

According to the present invention this object is solved by providing the T-cell receptor chain or T-cell receptor of the present invention, the soluble T-cell receptor construct of the present invention, the chimeric T-cell receptor of the present invention, the nucleic acid of the present invention, the expression construct of the present invention or the host cell of the present invention for use in the detection, prevention and/or treatment of influenza/influenza infections.

According to the present invention this object is solved by a method of preventing and/or treating influenza/influenza infections, comprising the steps of
(a) providing lymphocytes of a patient or a blood donor;
(b) providing one or more of
    (i) a T-cell receptor chain or T-cell receptor of the present invention or a chimeric T-cell receptor of the present invention,
    (ii) a nucleic acid of the present invention,
    (iii) an expression construct of the present invention,
    (iv) a cell of the present invention, and
    (v) a pharmaceutical composition of the present invention,
(c) ex vivo introduction of one or more of (i) to (v) of step (b) into the lymphocytes of step (a) and, thereby, obtaining genetically modified lymphocytes,
(d) administering the genetically modified lymphocytes of step (c) to a subject or patient in need thereof.

According to the present invention this object is solved by a method of detecting, preventing and/or treating influenza/influenza infections, comprising the detection and/or destruction of influenza-infected cells of a patient with the use of the soluble T-cell receptor construct according to the present invention.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "1 to 4 amino acids" should be interpreted to include not only the explicitly recited values of 1 and 4 amino acids, but also include individual values and sub-ranges within the indicated range. Thus, included in this numerical range are individual values such as 1, 2, 3 and 4 and sub-ranges such as from 1 to 3 amino acids and 2 to 4 amino acids etc. This same principle applies to ranges reciting only one numerical value. Furthermore, such an interpretation should apply regardless of the breadth of the range or the characteristics being described.

Influenza-Specific T-Cell Receptor

The invention relates to T-cell receptors and/or chains binding to the influenza matrix peptide GILGFVFTL (GL9 peptide) (SEQ ID NO. 9) presented by Human Leukocyte antigen A2 (HLA-A2) molecules.

As discussed above, the present invention provides an influenza-specific T-cell receptor a-chain and β-chain and a T-cell receptor comprising said α-chain and/or β-chain.

A majority of T cells have a T cell receptor (TCR) existing as a complex of several proteins. The actual T cell receptor is composed of two separate peptide chains, which are produced from the independent T cell receptor alpha and beta (TCR α and TCR β) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

The structure of the T cell receptor is very similar to immunoglobulin Fab fragments, which are regions defined as the combined light and heavy chain of an antibody arm. Each chain of the TCR is a member of the immunoglobulin superfamily and possesses one N-terminal immunoglobulin (Ig)-variable (V) domain, one Ig-constant (C) domain, a transmembrane/cell membrane-spanning region, and a short cytoplasmic tail at the C-terminal end.

According to the invention, the term "variable region of a T cell receptor" relates to the variable domains of the TCR chains.

The variable domain of both the TCR α-chain and β-chain have three hypervariable or complementarity determining regions (CDRs), whereas the variable region of the β-chain has an additional area of hypervariability (HV4) that does not normally contact antigen and therefore is not considered a CDR. CDR3 is the main CDR responsible for recognizing processed antigen, although CDR1 of the α-chain has also been shown to interact with the N-terminal part of the antigenic peptide, whereas CDR1 of the β-chain interacts with the C-terminal part of the peptide. CDR2 is thought to recognize the MHC. CDR4 of the β-chain is not thought to participate in antigen recognition, but has been shown to interact with superantigens.

The first signal in activation of T cells is provided by binding of the T cell receptor to a short peptide presented by the major histocompatibility complex (MHC) on another cell. This ensures that only a T cell with a TCR specific to that peptide is activated. Virus-specific CD8+ T-cells recognize usually 8-10 amino acid long virus-derived peptides bound to MHC class I molecules presented on the surface of virus-infected cells. The viral peptides are derived from viral proteins which are processed by proteasomes within the cytoplasma of infected cells. The peptides presented to CD4+ T cells by MHC class II molecules are longer, as the ends of the binding cleft of the MHC class II molecule are open. CD4+ T-cells usually recognize peptide-MHC class II complexes on the surface of professional antigen presenting cell (APC) such as dendritic cells, B cells and macrophages.

HLA A2+human subjects can generate CTL against the HLA-A2-restricted epitope GILGFVFTL (GL9) (SEQ ID NO. 9), which is located in the influenza matrix protein. The GL9-specific CTL response is dominated by T cell receptors (TCRs) of the Vβ17 clonotype (Lehner 1995), although other TCR Vβclonotypes can be used for generation of GL9-specific TCR (Petrova 2012). Despite the dominance of Vβ17clonotypes, there is a polyclonal heterogeneity within TCR consisting of Vβ17 clonotypes both with regard to the CDR3 sequence of the TCRβ-chain and with regard to the use of TCR alpha Vαclonotypes (Clute et al, 2010; Petrova 2012). Verra et al. (2004) describe tumor growth inhibition by hTER-transduced T cells. Thereby, they describe CTLs which specifically recognize the influenza matrix protein 58-66 (GILGFVFTL; SEQ ID NO. 9) on HLA-A2-positive cells.

The inventors have now identified an influenza-specific TCR which specifically recognizes the GILGFVFTL epitope (SEQ ID NO. 9) which is highly conserved in all influenza viruses, including swine influenza viruses and avian influenza viruses (bird flu). The respective epitopes/peptides of the different influenza viruses are all recognized by the TCR of the present invention.

As discussed above, the present invention provides a T-cell receptor α-chain or a T-cell receptor comprising said T-cell receptor α-chain, wherein said T-cell receptor α-chain comprises or consists of the amino acid sequence of SEQ ID NO. 1 (variable CDR3)

or an amino acid sequence that has at least 80% identity to the amino acid sequence of SEQ ID NO. 1, more preferably at least 85% identity, more preferably 90% identity or 95% identity (wherein at least 80% identity refers to changes in up to 4 amino acid residues of SEQ ID NO. 1, at least 85% identity refers to changes in up to 3 amino acid residues of SEQ ID NO. 1, at least 90% identity refers to changes in up to 2 amino acid residues of SEQ ID NO. 1 and at least 95% identity refers to changes in up to 1 amino acid residue of SEQ ID NO. 1), or any variation of the TCR sequence provided that said variation retains its functional ability to bind to the GL9/HLA-A2-complex.

The present invention provides a T-cell receptor α-chain or a T-cell receptor comprising said T-cell receptor α-chain, wherein said T-cell receptor α-chain comprises or consists of the amino acid sequence of SEQ ID NO. 1 (variable CDR3), or an amino acid sequence that has at least 80% identity to the amino acid sequence of SEQ ID NO. 1, more preferably at least 85% identity, more preferably 90% or 95% identity, provided that said amino acid sequence has the functional ability to bind to the GL9/HLA-A2-complex.

In one embodiment, said T-cell receptor α-chain comprises or consists of an amino acid sequence that has at least 95% or more than 95% identity to the amino acid sequence of SEQ ID NO. 1 (i.e. changes in up to 1 amino acid residue of SEQ ID NO. 1), provided that said amino acid sequence has the functional ability to bind to the GL9/HLA-A2-complex.

The terms "any variation of the TCR sequence provided that the biological activity is retained" or "any variation of the TCR sequence provided that said variation retains its functional ability to bind to the GL9/HLA-A2-complex" as interchangeably used herein refers to amino acid sequences of the TCR chain(s)/receptor(s) of the present invention that retain their functional activity with regard to TCR recognition of the GL9 peptide bound to the HLA A2-molecule.

The "biological activity", thus, refers to the recognition/binding of the GL9 peptide and its variants bound to HLA A2 by the TCR chain(s)/receptor(s) of the present invention.

Preferably, the T-cell receptor α-chain comprises or consists of the amino acid sequence of SEQ ID NO. 2 (full length)

or an amino acid sequence that has at least 85% identity to the amino acid sequence of SEQ ID NO. 2, more preferably at least 90% identity, more preferably 95% or 99% identity, or any variation of the TCR sequence provided that said variation retains its functional ability to bind to the GL9/HLA-A2-complex.

Preferably, the T-cell receptor α-chain comprises or consists of the amino acid sequence of SEQ ID NO. 2 (full length), or an amino acid sequence that has at least 85% identity to the amino acid sequence of SEQ ID NO. 2, more preferably at least 90% identity, more preferably 95% or 99% identity, provided that said amino acid sequence has the functional ability to bind to the GL9/HLA-A2-complex.

SEQ ID NO. 1 shows the amino acid sequence of the CDR3 variable region of the T-cell receptor α-chain which is mainly responsible for recognizing the specific influenza epitope:

LNTNAGKSTFGDGTTLTVKP

SEQ ID NO. 2 shows the full length amino acid sequence of the T-cell receptor α-chain (wherein SEQ ID NO. 1 is underlined):

MASAPISMLAMLFTLSGLRAQSVAQPEDQVNVAEGNPLTVKCTYSVSGNP

YLFWYVQYPNRGLQFLLKYITGDNLVKGSYGFEAEFNKSQTSFHLKKPSA

LVSDSALYFCAVRD<u>LNTNAGKSTFGDGTTLTVKP</u>NIQNPDPAVYQLRDSK

SSDKSVCLFTDFDSQTNVSQSKDSDVYITDKTVLDMRSMDFKSNSAVAWS

NKSDFACANAFNNSIIPEDTFFPSPESSCDVKLVEKSFETDTNLNFQNLS

VIGFRILLLKVAGFNLLMTLRLWSS

As discussed above, the present invention provides a T-cell receptor β-chain or a T-cell receptor comprising said T-cell receptor β-chain, wherein said T-cell receptor β-chain comprises or consists of the amino acid sequence of SEQ ID NO. 3 (variable CDR3)

or an amino acid sequence that has at least 77% identity to the amino acid sequence of SEQ ID NO. 3, more preferably at least 83% identity, more preferably 88% or 94% identity, (wherein at least 77% identity refers to changes in up to 4 amino acid residues of SEQ ID NO. 3, at least 83% identity refers to changes in up to 3 amino acid residues of SEQ ID NO. 3, at least 88% identity refers to changes in up to 2 amino acid residues of SEQ ID NO. 3 and at least 94% identity refers to changes in up to 1 amino acid residue of SEQ ID NO. 3), or any variation of the TCR sequence provided that said variation retains its functional ability to bind to the GL9/HLA-A2-complex.

The present invention provides a T-cell receptor β-chain or a T-cell receptor comprising said T-cell receptor β-chain, wherein said T-cell receptor β-chain comprises or consists of the amino acid sequence of SEQ ID NO. 3 (variable CDR3), or an amino acid sequence that has at least 77% identity to the amino acid sequence of SEQ ID NO. 3, more preferably at least 83% identity, more preferably 88% or 94% identity, provided that said amino acid sequence has the functional ability to bind to the GL9/HLA-A2-complex.

In one embodiment, said T-cell receptor β-chain comprises or consists of an amino acid sequence that has at least 83% or more than 83% identity, such as at least 88% or at least 94% identity, to the amino acid sequence of SEQ ID NO. 3 (i.e. changes in up to 3 or 2 or 1 amino acid residue of SEQ ID NO. 3), provided that said amino acid sequence has the functional ability to bind to the GL9/HLA-A2-complex.

Preferably, the T-cell receptor β-chain comprises or consists of the amino acid sequence of SEQ ID NO. 4 (full length)

or an amino acid sequence that has at least 85% identity to the amino acid sequence of SEQ ID NO. 4, more preferably at least 90% identity, more preferably 95% or 99% identity, or any variation of the TCR sequence provided that said variation retains its functional ability to bind to the GL9/HLA-A2-complex.

Preferably, the T-cell receptor β-chain comprises or consists of the amino acid sequence of SEQ ID NO. 4 (full length), or an amino acid sequence that has at least 85% identity to the amino acid sequence of SEQ ID NO. 4, more preferably at least 90% identity, more preferably 95% or 99% identity, provided that said amino acid sequence has the functional ability to bind to the GL9/HLA-A2-complex.

SEQ ID NO. 3 shows the amino acid sequence of the CDR3 variable region of the T-cell receptor β-chain which is mainly responsible for recognizing the specific influenza epitope:

TSGTEAFFGQGTRLTVV

SEQ ID NO. 4 shows the full length amino acid sequence of the T-cell receptor β-chain (wherein SEQ ID NO. 3 is underlined):

MSNQVLCCVVLCFLGANTVDGGITQSPKYLFRKEGQNVTLSCEQNLNHDA

MYWYRQDPGQGLRLIYYSQIVNDFQKGDIAEGYSVSREKKESFPLTVTSA

QKNPTAFYLCASSSTSGTEAFFGQGTRLTVVEDLNKVFPPEVAVFEPSEA

EISHTQKATLVCLATGFFPDHVELSWWVNGKEVHSGVSTDPQPLKEQPAL

NDSRYCLSSRLRVSATFWQNPRNHFRCQVQFYGLSENDEWTQDRAKPVTQ

IVSAEAWGRADCGFTSVSYQQGVLSATILYEILLGKATLYAVLVSALVLM

AMVKRKDF

As discussed above, the present invention provides a T-cell receptor comprising:
(i) a T cell receptor α-chain comprising or consisting of the amino acid sequence of the amino acid sequence of LNTNAGKSTFGDGTTLTVKP (variable CDR3) (SEQ ID NO. 1) or SEQ ID NO. 2 (full length)
or an amino acid sequence that has at least 80% identity to the amino acid sequence of SEQ ID NO. 1, more preferably at least 85% identity, more preferably 90% identity or 95% identity,
or an amino acid sequence that has at least 85% identity to the amino acid sequence of SEQ ID NO. 2, more preferably at least 90% identity, more preferably 95% or 99% identity,
or any variation of the TCR sequence provided that said variation retains its functional ability to bind to the GL9/HLA-A2-complex,
and
(ii) a T-cell receptor β-chain comprising or consisting of the amino acid sequence of TSGTEAFFGQGTRLTVV (variable CDR3) (SEQ ID NO. 3) or SEQ ID NO. 4 (full length)
or an amino acid sequence that has at least 77% identity to the amino acid sequence of SEQ ID NO. 3, more preferably at least 83% identity, more preferably 88% or 94% identity,
or an amino acid sequence that has at least 85% identity to the amino acid sequence of SEQ ID NO. 4, more preferably at least 90% identity, more preferably 95% or 99% identity,
or any variation of the TCR sequence provided that said variation retains its functional ability to bind to the GL9/HLA-A2-complex.

The present invention provides a T-cell receptor comprising:
(i) a T cell receptor α-chain comprising the amino acid sequence of SEQ ID NO. 1 or SEQ ID NO. 2
or an amino acid sequence that has at least 80% identity to the amino acid sequence of SEQ ID NO. 1 or an amino acid sequence that has at least 85% identity to the amino acid sequence of SEQ ID NO. 2, provided that said amino acid sequence has the functional ability to bind to the GL9/HLA-A2-complex,
and
(ii) a T-cell receptor β-chain comprising the amino acid sequence of SEQ ID NO. 3 or SEQ ID NO. 4
or an amino acid sequence that has at least 77% identity to the amino acid sequence of SEQ ID NO. 3 or an amino acid sequence that has at least 85% identity to the amino acid sequence of SEQ ID NO. 4, provided that said amino acid sequence has the functional ability to bind to the GL9/HLA-A2-complex.

Soluble TCR (sTCR) Constructs

As discussed above, the present invention provides soluble T-cell receptor (sTCR) constructs comprising the T-cell receptors/chains of the present invention.

Said soluble T-cell receptor (sTCR) constructs comprise
(1) at least one of
T-cell receptor α-chain(s) of the present invention,
T-cell receptor β-chain(s) of the present invention,
that are preferably covalently linked to each other to form TCR heterodimers or multimers, and
(2) fusion component(s)
preferably selected from
Fc receptors and/or Fc domains,
cytokines, such as IL-2 or IL-15,
toxins, such as exotoxin A, *Pseudomonas* exotoxin,
antibodies, such as anti-CD3-antibodies
or combinations thereof,
wherein the at least one T-cell receptor chain (1) is covalently bound to the fusion component(s) (2).

Preferably, the soluble T-cell receptor comprises furthermore labels, such as radionuclides, fluorophors (such as fluorescein), which are preferably covalently attached/coupled to the soluble TCR, such as to the fusion component(s) (2).

In one embodiment, the soluble T-cell receptor comprises as fusion component (2) IL-15 multimers. Such soluble TCRs are, for example, described in WO 2008/143794 A1 and WO 2012/040323 A2 (both of Altor Bioscience Corp.).

For example, a soluble TCR can comprise as fusion component (2) IL-15 multimers, such as two IL-15 domains which are linked/bound together and wherein each IL-15 domain is bound to a T-cell receptor α-chain(s) and/or T-cell receptor β-chain(s) of the present invention.

The soluble TCRs can comprise different of the fusion components (2), such as IL-15 and Fc domains. See for example, WO 2012/040323 A2.

TCR-alpha- and TCR-beta-chains can be solubilized by chemical modifications and linked covalently to each other and to other molecules such as Fc-receptors, cytokines and toxins (as described in Boulter et al, 2005; Lunde et al 2010).

These soluble TCR constructs are suitable to be directly used for the detection and destruction of influenza-infected cells without the need of T-cells. This can be achieved by application of soluble T-cell receptor constructs to patients by intravenous, subcutaneous or intramuscular infusion or injections, respectively, or by application to the mucosa of the respiratory tract by inhalation or by spraying.

Chimeric TCRs

As discussed above, the present invention provides chimeric T-cell receptors comprising at least one of
  the T-cell receptor α-chain of the present invention,
  the T-cell receptor β-chain of the present invention, or
  the T-cell receptor of the present invention,
wherein the TCR α-chain and/or the TCR β-chain is/are
  fused to CD3-zeta chain(s), preferably via a linker.

In one embodiment, a chimeric TCR of the invention comprises the T-cell receptor α-chain of the invention and the T-cell receptor β-chain of the invention, which are fused to each other via a linker and which are furthermore fused to CD3-zeta chain(s).

Preferred CD3-zeta chain(s) are the zeta-chain(s) of the human CD3 complex of the T-cell receptor.

The chimeric TCRs can comprise further components.

Chimeric T-cell receptors and chimeric antigen receptors (CAR) are known in the art. See, for example, Han et al. 2013.

Nucleic Acids, Expression Constructs and Cells Comprising the Influenza-Specific TCR As discussed above, the present invention provides a nucleic acid encoding the T-cell receptor chain or T-cell receptor according to the present invention.

Preferably, the nucleic acid comprises
  the nucleic acid encoding for the amino acid sequence of SEQ ID NO. 1 and/or 3
    or the nucleotide sequence of SEQ ID NO. 5 and/or 7
    or their complementary sequence(s)
    or sequence(s) that have at least 80% identity to the nucleotide sequence of SEQ ID NO. 5 or 7, more preferably at least 85% identity, more preferably 90% identity or 95% identity or 99% identity.

In one embodiment, the nucleic acid comprises or consists of nucleotide sequence(s) that have a difference in up to 7 nucleotides of the nucleotide sequence of SEQ ID NO. 5 and/or 7.

SEQ ID NO. 5 shows the nucleotide sequence of the CDR3 variable region of the T-cell receptor α-chain which is mainly responsible for recognizing the specific influenza epitope:

TTAACACCAATGCAGGCAAATCAACCTTTGGGGATGGGACTACGCTCACT
GTGAAGCCAA

SEQ ID NO. 7 shows the nucleotide sequence of the CDR3 variable region of the T-cell receptor β-chain which is mainly responsible for recognizing the specific influenza epitope:

ATCGGGCACTGAAGCTTTCTTTGGACAAGGCACCAGACTCACAGTTGTA

In one embodiment, the nucleic acid comprises
  the nucleic acid encoding for the amino acid sequence of SEQ ID NO. 2 and/or 4
    the nucleotide sequence of SEQ ID NO. 6 and/or 8
    or their complementary sequence(s)
    or sequence(s) that have at least 80% identity to the nucleotide sequence of SEQ ID NO. 6 or 8, more preferably at least 85% identity, more preferably 90% identity or 95% identity or 99% identity.

SEQ ID NO. 6 shows the full length nucleotide sequence of the T-cell receptor α-chain (wherein SEQ ID NO. 5 is underlined):

ATGGCCTCTGCACCCATCTCGATGCTTGCGATGCTCTTCACATTGAGTGG

GCTGAGAGCTCAGTCAGTGGCTCAGCCGGAAGATCAGGTCAACGTTGCTG

AAGGGAATCCTCTGACTGTGAAATGCACCTATTCAGTCTCTGGAAACCCT

TATCTTTTTTGGTATGTTCAATACCCCAACCGAGGCCTCCAGTTCCTTCT

GAAATACATCACAGGGGATAACCTGGTTAAAGGCAGCTATGGCTTTGAAG

CTGAATTTAACAAGAGCCAAACCTCCTTCCACCTGAAGAAACCATCTGCC

CTTGTGAGCGACTCCGCTTTGTACTTCTGTGCTGTGAGAGAT<u>TTAACAC</u>

<u>CAATGCAGGCAAATCAACCTTTGGGGATGGGACTACGCTCACTGTGAAGC</u>

<u>CAA</u>ATATCCAGAACCCTGACCCTGCCGTGTACCAGCTGAGAGACTCTAAA

TCCAGTGACAAGTCTGTCTGCCTATTCACCGATTTTGATTCTCAAACAAA

TGTGTCACAAAGTAAGGATTCTGATGTGTATATCACAGACAAAACTGTGC

TAGACATGAGGTCTATGGACTTCAAGAGCAACAGTGCTGTGGCCTGGAGC

AACAAATCTGACTTTGCATGTGCAAACGCCTTCAACAACAGCATTATTCC

AGAAGACACCTTCTTCCCCAGCCCAGAAAGTTCCTGTGATGTCAAGCTGG

TCGAGAAAAGCTTTGAAACAGATACGAACCTAAACTTTCAAAACCTGTCA

GTGATTGGGTTCCGAATCCTCCTCCTGAAAGTGGCCGGGTTTAATCTGCT

CATGACGCTGCGGCTGTGGTCCAGC

SEQ ID NO. 8 shows the full length nucleotide sequence of the T-cell receptor β-chain (wherein SEQ ID NO. 7 is underlined):

ATGAGCAACCAGGTGCTCTGCTGTGTGGTCCTTTGTTTCCTGGGAGCAAA

CACCGTGGATGGTGGAATCACTCAGTCCCCAAAGTACCTGTTCAGAAAGG

AAGGACAGAATGTGACCCTGAGTTGTGAACAGAATTTGAACCACGATGCC

ATGTACTGGTACCGACAGGACCCAGGGCAAGGGCTGAGATTGATCTACTA

CTCACAGATAGTAAATGACTTTCAGAAAGGAGATATAGCTGAAGGGTACA

GCGTCTCTCGGGAGAAGAAGGAATCCTTTCCTCTCACTGTGACATCGGCC

CAAAAGAACCCGACAGCTTTCTATCTCTGTGCCAGTAGTTCTAC<u>ATCGGG</u>

<u>CACTGAAGCTTTCTTTGGACAAGGCACCAGACTCACAGTTGTA</u>GAGGACC

TGAACAAGGTGTTCCCACCCGAGGTCGCTGTGTTTGAGCCATCAGAAGCA

GAGATCTCCCACACCCAAAAGGCCACACTGGTGTGCCTGGCCACAGGCTT

CTTCCCTGACCACGTGGAGCTGAGCTGGTGGGTGAATGGGAAGGAGGTGC

ACAGTGGGGTCAGCACAGACCCGCAGCCCCTCAAGGAGCAGCCCGCCCTC

AATGACTCCAGATACTGCCTGAGCAGCCGCCTGAGGGTCTCGGCCACCTT

CTGGCAGAACCCCCGCAACCACTTCCGCTGTCAAGTCCAGTTCTACGGGC

TCTCGGAGAATGACGAGTGGACCCAGGATAGGGCCAAACCCGTCACCCAG

ATCGTCAGCGCCGAGGCCTGGGGTAGAGCAGACTGTGGCTTTACCTCGGT

GTCCTACCAGCAAGGGGTCCTGTCTGCCACCATCCTCTATGAGATCCTGC

TAGGGAAGGCCACCCTGTATGCTGTGCTGGTCAGCGCCCTTGTGTTGATG

GCCATGGTCAAGAGAAAGGATTTC

The nucleotide sequences of SEQ ID NO. 7 and 8 are cDNA.

As discussed above, the present invention provides a nucleic acid encoding the soluble T-cell receptor construct according to the present invention.

As discussed above, the present invention provides a nucleic acid encoding the chimeric T-cell receptor according to the present invention.

The nucleic acids according to this invention comprise DNA (such as dsDNA, ssDNA, cDNA), RNA (such as dsRNA, ssRNA, mRNA), combinations thereof or derivatives (such as PNA) thereof.

Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the same amino acids as the codons that are being exchanged.

Within the scope of this invention are also the nucleotide sequences obtained due to the degeneration of the genetic code of the above nucleotide sequences.

As discussed above, the present invention provides an expression construct for expressing the T-cell receptor chain or T-cell receptor according to the present invention in a cell.

As discussed above, the present invention provides an expression construct for expressing the soluble T-cell receptor construct according to the present invention in a cell.

As discussed above, the present invention provides an expression construct for expressing the chimeric T-cell receptor according to the present invention in a cell.

Preferably, the expression constructs further comprise promoter and terminator sequences.

An "expression or gene construct" (wherein both terms are used interchangeably throughout this specification) refers to a nucleic acid construct, usually an expression vector or plasmid, that is used to introduce a specific gene sequence into a target cell. Once the expression or gene construct is inside the cell, the protein that is encoded by the gene is produced by the cellular transcription and translation machinery. The expression or gene construct is designed to contain respective regulatory sequences that act as enhancer and promoter regions and lead to efficient transcription of the gene carried on the construct, including promoter and terminator sequences. The goal of a well-designed expression or gene construct is the production of large amounts of stable mRNA, and therefore proteins.

The skilled artisan can select further suitable components of expression or gene constructs.

Examples for suitable expression constructs are mRNA-constructs (Hofmann et al., 2011) or plasmids (as described in Nakazawa et al, 2011) that can be introduced into the cell by electroporation or by transfection reagents, such as liposomes. Further examples for suitable expression constructs are viral vectors, such as retroviral vectors (as described in Verra et al, 2004; Porter et al, 2011) and lentiviral vectors (as described in Josef et al, 2008). Viral vectors containing TCR-encoding genes can infect lymphocytes and express functional TCR in infected lymphocytes.

The nucleic acids and/or in particular expression constructs of the invention are capable of directing the synthesis/expression of the TCR chain(s) or TCRs of the invention in a suitable host cell.

As discussed above, the present invention provides a cell comprising the T-cell receptor chain or T-cell receptor according to the present invention or the soluble T-cell receptor construct according to the present invention or the chimeric T-cell receptor of the invention or the nucleic acid(s) of the present invention or the expression construct of the present invention.

Preferably, the cell expresses the T-cell receptor chain or T cell-receptor of the present invention.

Preferably, the cell expresses the chimeric T-cell receptor according to the present invention.

Preferably, the cell is selected from lymphocytes including but not limited to CD8+T alpha/beta-lymphocytes (CTLs), CD4+ T cells, natural killer (NK) cells, natural killer T (NKT) cells, gamma/delta-T-cells.

The transfer of influenza-specific TCR genes into (primary) T cells by e.g. viral vectors represents a promising means and method to generate influenza antigen-specific T cells. Adoptive transfer of such engineered T cells into hosts represents a promising approach for the immunotherapy of influenza.

Pharmaceutical Compositions

As discussed above, the present invention provides a pharmaceutical composition comprising one or more of:
(i) the T-cell receptor α-chain of the present invention;
(ii) the T-cell receptor β-chain of the present invention;
(iii) the T-cell receptor of the present invention;
(iv) the soluble T-cell receptor construct of the present invention;
(v) the chimeric T-cell receptor of the present invention;
(vi) the nucleic acid(s) of the present invention or the expression construct of the present invention; and/or
(vii) the cell of the present invention,
and, optionally, pharmaceutically excipient(s).

Medical Uses of the Influenza-Specific TCR

As discussed above, the present invention provides the use of a T-cell receptor chain or T-cell receptor of the present invention, a chimeric T-cell receptor, a nucleic acid of the present invention or an expression construct of the present invention for generating genetically modified lymphocytes.

Preferably the genetically modified lymphocytes are T cells, NK cells and/or NKT cells.

In one embodiment, the generated genetically modified lymphocytes, preferably T cells and/or NK cells, are used for genetic immunization, preferably for preventing and/or treating influenza/influenza infections.

The transfer of influenza-specific TCR genes into (primary) T cells by e.g. viral vectors represents a promising means and method to generate influenza antigen-specific T cells. Adoptive transfer of such engineered T cells into hosts represents a promising approach for the immunotherapy of influenza.

In one embodiment, the chimeric T-cell receptor(s) of the present invention are used to generate genetically modified lymphocytes, preferably NK cells.

The transfer of chimeric receptors containing the whole or parts of the influenza-specific TCR genes linked to the CD3 zeta chain into primary NK cells by e.g. viral vectors represents a promising means and method to generate influenza antigen-specific NK cells. Adoptive transfer of such engineered NK cells into hosts represents a promising approach for the immunotherapy of influenza.

As discussed above, the present invention provides the T-cell receptor chain or T-cell receptor of the present invention, the nucleic acid of the present invention, the expression construct of the present invention or the host cell of the present invention for use as a medicament.

As discussed above, the present invention provides the T-cell receptor chain or T-cell receptor of the present invention, the nucleic acid of the present invention, the expression construct of the present invention or the host cell of the present invention for use in the prevention and/or treatment of influenza/influenza infections.

Preferably, the use comprises adoptive, target-cell specific immunotherapy or genetic immunization.

The patients are preferably HLA2-positive.

Method of Preventing and/or Treating Influenza

As discussed above, the present invention provides a method of preventing and/or treating influenza/influenza infections.

Said method comprises the steps of
(a) providing lymphocytes of a patient or a blood donor;
(b) providing one or more of
  (i) a T-cell receptor chain or T-cell receptor of the present invention,
  (ii) a nucleic acid of the present invention,
  (iii) an expression construct of the present invention,
  (iv) a cell of the present invention, and
  (v) a pharmaceutical composition of the present invention,
(c) ex vivo introduction of one or more of (i) to (v) of step (b) into the lymphocytes of step (a) and, thereby, obtaining genetically modified lymphocytes,
(d) administering the genetically modified lymphocytes of step (c) to a subject or patient in need thereof.

The subjects or patients are preferably HLA2-positive.

The subjects or patients are either infected with influenza or healthy.

Preferably, the lymphocytes provided in step (a) are T cells, NK cells and/or NKT cells, preferably CD8+ T cells.

T cell receptors consisting of T cell receptor alpha and beta chains are used for transduction of T cells and NKT cells. For transduction of NK-cells, the T-cell receptor or single TCR-alpha- and/or TCR-beta chains are provided as a chimeric receptor, where the TCR is for example linked to the CD3zeta chain. See, for example, Zhang et al. 2013.

The lymphocytes provided in step (a) can be obtained from the subject or patient, such as from the blood or by lymphapheresis of allogeneic blood donors.

Preferably, the ex vivo introduction in step (c) is carried out via electroporation of a nucleic acid of the present invention or of an expression construct of the present invention, or by transfection reagents, such as liposomes.

The expression construct is preferably
an mRNA construct
  encoding the TCR-alpha- or TCR-beta chains;
or
a viral construct,
  preferably a lentiviral vector, retroviral vector, or other state of the art viral vector.

In one embodiment, the method further comprises the following step
  increasing the lytic ability of the genetically modified lymphocytes.

The time at which said further step is carried out in the method of the invention depends on the expression vector or construct used and/or on the ex vivo introduction of step (c). Usually, it is preferred to activate the cells and then carry out the ex vivo introduction (see step (c)).

In an embodiment, where mRNA electroporation is used, the activation/increasing the lytic ability is carried out after the ex vivo introduction.

In an embodiment, where retroviral vectors and transduction are used, the activation/increasing the lytic ability is carried out before the ex vivo introduction.

In an embodiment, where lentiviral vectors are used, the activation/increasing the lytic ability can be carried out before and after the ex vivo introduction.

The lytic ability of the genetically modified lymphocytes can be activated in vitro by
  mitogens, such as OKT 3, PHA
  and/or
  cytokines, such as Interleukin-2 (such as with doses of about 1 to 1000 U/ml) and/or Interleukin-7 (such as with doses of about 1 to 1000 U/l) and/or Interleukin-15.

As discussed above, the present invention provides a method of detecting, preventing and/or treating influenza/influenza infections, comprising the detection and/or destruction of influenza-infected cells of a patient with the use of the soluble T-cell receptor construct of the present invention.

Preferably, the soluble T-cell receptor constructs are applied to patients by intravenous, subcutaneous or intramuscular infusion or injections, respectively, or by application to the mucosa of the respiratory tract by inhalation or by spraying.

Soluble T-cell receptor constructs can be applied to patients:
  by intravenous infusions,
  by subcutaneous injection or infusion,
  by intramuscular injection,
  by inhalation or by spraying to the mucosal surfaces of the respiratory tract.

Suitable dose ranges for application of soluble T-cell receptor constructs vary between 1 mg to 10 000 mg dependent on the application method and application site. Soluble T-cell receptors can bind to cells expressing GL9 peptides on their HLA-A2 molecules. Soluble T-cell receptors can induce destruction of the cells via different methods, such as radiation by linked radionuclides or killing by toxins such as *pseudomonas* exotoxin. In addition, soluble T-cell receptors with linked Fc-domains can redirect and activate NK-cells and/or monocytes for the lysis of influenza infected cells. Similarly, soluble T-cell receptors linked to anti-CD3-antibodies can redirect and activate T-cells for lysis of influenza infected cells.

In one embodiment the method of the invention is for detecting influenza/influenza infections, comprising the in vitro staining of influenza-virus infected cells by using the soluble T-cell receptor construct of the present invention which are labelled.

The label can be fluorophor(s) and/or radionuclide(s).

Soluble T-cell receptors linked to fluorescent molecules such as fluorescein can be used to stain influenza virus infected cells in vitro. For this purpose, influenza virus infected cells are incubated in vitro with the soluble T-cell receptor constructs, and infected cells expressing HLA-A2/GL9-complexes on the cell surface can be detected according to their fluorescence by a Fluorescence activated cell sorter (FACS) or by microscope.

The soluble TCR-constructs of the invention are suitable to be directly used for the detection and destruction of influenza-infected cells without the need of T-cells.

The subjects or patients are preferably HLA2-positive.

Further Description of a Preferred Embodiment

The inventors have generated the Influenza matrix protein-specific TCR by isolating the TCR-encoding cDNA from an influenza specific CTL line that could recognize the HLA-A2-restricted influenza-matrix epitope GILGFVFTL (GL9) (SEQ ID NO. 9). The CTL line was obtained by in vitro culture of peptide stimulated peripheral blood mononuclear cells derived from an HLA-A2 positive healthy subject. The whole mRNA was isolated from the CTL line, reverse-transcribed into cDNA and amplified with TCR-specific primers. After cloning of the TCR-alpha- and TCR-beta-chains, TCR-encoding mRNA was produced by in vitro transcription. The specificity of this TCR was demonstrated by electroporation of two mRNA-constructs encoding the TCR-alpha or the TCR-beta-chain of the influenza-specific TCR into T-cells from blood donors. The expression of the GILGFVFTL (SEQ ID NO. 9)-specific TCR on the cell surface of electroporated T-cells could be proven by staining with a dextrarner specific for the GILGFVFTL -peptide. The functional activity of TCR-electroporated T-cells could be demonstrated in gamma-IFN ELISPOT assays. In the ELISPOT assay, antigen-specific T-cells are detected via the secretion of gamma-IFN after stimulation with the cognate peptide.

The GL9-epitope recognized by the TCR of the present invention is highly conserved between all mammal and avian influenza viruses. Because of the widespread animal reservoir of influenza viruses, there is an ongoing threat of the emergence of new highly pathogenic human influenza viruses that develop by mutations or reassortments of different mammal and avian influenza viruses. Gene therapy with genetic immunization via the transfer of the GL9-specific TCR could provide protection from new influenza viruses against which there is no vaccine yet available.

The TCR-constructs of the present invention can be used both for therapy and prevention of influenza virus-infection in HLA-A2-positive patients. In Europe, approximately 40% of subjects are HLA-A2-positive.

The TCR-constructs of the present invention can be used for treatment of patients already infected by influenza-viruses. The GL9-specific TCR can be transferred into lymphocytes, especially in CD8+ T-cells, via electroporation of lymphocytes with TCR-encoding mRNA- or DNA-constructs. Alternatively, the TCR can be transferred into lymphocytes using transfection reagents, such as liposomes or TCR-expressing viral vectors, such as retroviral or lentiviral vectors. The transfection of the GL9-specific TCR into CD8+ T-cells and in to gamma-delta-T-cells generates CTL capable to kill influenza virus infected cells. The transfection of the GL9-specific TCR into CD4+ T-cells generates CD4+ helper T-cells which usually do not kill infected cells but which can improve the influenza-specific immune response by providing help through secretion of cytokines. In addition, the transfection of chimeric GL9-specific TCR linked to other molecules, such as the CD3zeta-chain, can reprogram NK-cells for lysis of influenza virus infected cells.

Transfer of GL9-specific TCR into lymphocytes of influenza-uninfected subjects can be used for protection from influenza infections. Although influenza-specific CTL can not prevent infection of cells by influenza viruses, they can control the spread of viral infection by elimination of infected cells. Thereby, they can prevent the development of clinical symptoms and diseases by influenza viruses.

TCR-alpha- and TCR-beta-chains can be solubilized by chemical modifications and linked covalently to each other and to other molecules such as Fc-domains, cytokines, radionuclides and toxins (Boulter et al, 2005; Lunde et al 2010). These soluble TCR-constructs can directly be used for the detection and destruction of influenza-infected cells without the need of T-cells.

The following examples and drawings illustrate the present invention without, however, limiting the same thereto.

BRIEF DESCRIPTION OF THE DRAWINGS

FIG. 1. Stimulation of T cells.

Peripheral blood mononuclear cells (PBMC) of the blood donor EJ were electroporated with the influenza-specific T-cell receptor. The PBMC were then incubated with the HLA-A2-positive cell line T2 in a gamma-interferon-ELISPOT assay. The T2 cells were incubated with the influenza peptide IMP (GL9) or with the control peptide IV9. Mock are PBMC, which were electroporated without T-cell receptor genes. Shown is the number of cells which release gamma-interferon after contact with antigen (spot forming unit=SFU=number of the reactive T cells). As can be seen, the co-incubation of T2 cells which were incubated with the influenza IMP GL9-peptide, leads to a strong stimulation of T cells which were incubated with the influenza-specific T-cell receptor.

FIG. 2. Peptide titration of the influenza GL9 peptide.

The T2 cell line was incubated with serial dilutions of the influenza GL9 peptide. Then, the T2 cells ware incubated in the gamma-Interferon-ELISPOT assay with lymphocytes, which were re-programmed via electroporation with influenza TCR-coding mRNA (TCR EP). Thereby, the T cells were recognized at peptide concentrations as low as 50 ng/ml. IV9 is a control peptide, which is not recognized. Mock EP are lymphocytes which were electroporated without mRNA and thus do not express the influenza TCR.

FIG. 3. Sequence of the TCR alpha chain.

Nucleotide (SEQ ID NO. 6) and amino acid sequence (SEQ ID NO. 2) of the TCR alpha chain: Underlined is the CDR3 region containing the variable sequence, encoding for the specificity of the peptide (influenza epitope).

FIG. 4. Sequence of the TCR beta chain.

Nucleotide (SEQ ID NO. 8) and amino acid sequence (SEQ ID NO. 4) of the TCR beta chain: Underlined is the CDR3 region containing the variable sequence, encoding for the specificity of the peptide (influenza epitope).

EXAMPLES

Material and Methods

Isolation of PBMC and Generation of Specific Cytotoxic T Cell Lines

Peripheral blood mononuclear cells (PBMC) were obtained by Ficoll-Hypaque (Bio-Rad AG, Dreieich, Germany) density gradient centrifugation. For the generation of specific T cell lines, the PBMC were stimulated with the GL9 peptide at a final concentration of 6 μg/ml in 1 ml RPMI 1640 medium (Gibco Invitrogen, Karlsruhe, Germany) containing 10% heat-inactivated fetal bovine serum (FCS) (PAN Biotech GmbH, Aidenbach, Germany), 1% L-glutamine (2 mmol/1), penicillin (100 U/ml), streptomycin (100 μg/ml), Hepes (10 mmol/1) (Merck, Darmstadt, Germany) and 10 U/ml recombinant Interleukin-2 (Proleukin, Chiron, CA, USA). After 10 to 14 days, the outgrowing cells were tested for recognition of IMP-GL9 peptide. The specific CTL responses were analyzed by γ-Interferon enzyme-linked immunospot assays (ELISPOT). ELISPOT assays were conducted using R5AB media consisting of RPMI 1640 medium with supplements and 5% heat-inactivated human AB-Serum (Sigma-Aldreich, Steinheim, Germany).

Peptides

The Peptides IMP-GL9 (GILGFVFTL, SEQ ID NO. 9) and HIV-1 p17 SL9 (SLYNTVATL, SEQ ID NO. 10) were synthesized as C-terminal carboxamides (EMC Microcollections, Tübingen, Germany). Stock solutions of peptides were prepared in dimethyl sulfoxide (20 mg/ml, Merck, Darmstadt, Germany). For the assessment of the functional avidity of peptides by peptide titrations assays, peptides were added in serial dilutions ranging from 20 μg/ml to 1 ng/ml to ELISPOT plates and incubated with CD8+ T-cell lines for 18-48 hours.

ELISPOT Analysis 96-well, nitrocellulose, filter-backed microtiter plates (MultiScreen® HTS Filter Plates, Millipore, Molsheim, France) were activated with 20 μl/well 70% Methanol (Merck, Darmstadt, Germany), and after washing twice with PBS, the plates were coated with 50 μl of anti-human γ-Interferon (γ-IFN) antibody 1-D1K (Mabtech, Stockholm, Sweden) at a concentration of 10 μg/ml. After this, the plates were washed four times with PBS and blocked with R5AB. The plates could be stored at −20° C. until they were used. After thawing the cells were added. Four hours after electoporation 1-1.5×10$^5$ electroporated PBMC were analyzed in duplicates by ELISpot, while 0.5×10$^5$ stimulated T cells per well were used for analysis of the peptide specific responses. Peptides were added directly to the wells at a final concentration of 20 μg/ml. In addition, EBV-transformed B-lymphoblastoid cell lines (B-LCL) incubated with IMP-GL9 peptide (100 μg/ml) were used as antigen presenting cells. HLA-A2 positive B-LCL were incubated for one hour at 37° C. in 7% $CO_2$, washed three times with PBS and 0.5×10$^5$ B-LCL per well were added. The plates were incubated for 18-48 hours at 37° C. in 7% $CO_2$. After six washes with PBS containing 0.05% Tween 20 (PBS-T0.05%), 100 μl biotinylated anti-human γ-IFN monoclonal antibody 7-B6-1 (Mabtech, Stockholm, Sweden) was incubated at a final concentration of 2 μg/ml for two hours at room temperature. After washing six times with PBS-T0.05%, 100 μl avidin/peroxidase substrate (Vectastain® ABC-Kit, Linaris, Wertheim, Germany) was added to each well, the plates were incubated for one to three hours at room temperature and then washed three times with PBS-T0.05% and three times with PBS. Finally 100 μl AEC substrate (3-amino-9-ethylcarbazole, Sigma-Aldrich, Germany) containing 0.01% $H_2O_2$ was added as chromogen to each well. Spots developed within four minutes, and the reaction was stopped by washing the plates with distilled water. The plates were air-dried, and the spots were counted using the Elispot reader (AID, Strassberg, Germany).

Dextramer Staining

The generated T cells were stained with the SL9-specific MHC-Dextramer conjugated with PE (Immudex, Dako, Denmark), following the manufactures' instructions.

In brief, 2-5×10$^5$ T cells were washed with PBS containing 5% heat-inactivated FCS and were centrifuged at 300×g for 5 minutes. The supernatant was removed, and the cells were resuspended in the remaining liquid. 10 μl of MHC Dextramer were added, mixed, and incubated for 10 minutes at room temperature. 5 μl of anti-CD8 antibody (Beckman Coulter, Krefeld, Germany), conjugated either with FITC, was added and incubated for 20 minutes at 4° C. Afterwards, the cells were washed twice with PBS+5% FCS and resuspended in PBS. The measuring was done in a FACS cytometer (FACS Calibur, BD, Heidelberg, Germany). In addition, the cells were sorted in an Aria II FACS (BD, Heidelberg).

Electroporation of PBMC with mRNA

After isolation of PBMC by density centrifugation, 3-4× 10$^7$ PBMC were cultured in 10 ml RPMI1640 with 1% human AB serum, 1% L-glutamine (2 mmol/l), penicillin (100 U/ml), and streptomycin (100 μg/ml) in a 60 mm cell culture dish overnight under standard conditions (37° C., 7% $CO_2$). Then, PBMC were harvested from the dishes and washed with pure RPMI1640 and with Optimem (Gibco Invitrogen, Germany) both at room temperature. For electroporation 0.5-1×10$^7$ PBMC were resuspended in a volume of 100 μl Optimem. 15 μg of each TCR-chain mRNA were transferred into a 4 mm cuvette (Peqlab, Erlangen, Germany). Electroporation was performed with a Genepulser Xcell (Bio-Rad, Munich, Germany) with following pulse conditions: square wave pulse, 500 V, 3 ms. Immediately after electroporation, the cells were transferred into prewarmed RPMI1640 with 1% human AB serum, 1% L-glutamine (2 mmol/l), penicillin (100 U/ml), and streptomycin (100 μg/ml). For mock electroporation, no mRNA was added to the cells before electroporation.

Production of TCR-mRNA Constructs

Total RNA was isolated from GL9-specific CTL lines using the NucleoSpin® RNA II Kit (Machery-Nagel, Düren, Germany) according to the manufactures' instructions. Reverse transcription was conducted using the Superscript II Reverse transcriptase (Invitrogen, Darmstadt, Germany), 10 pmol of each

```
64T-primer
                                        (SEQ ID NO. 11)
CGATAAAAGCTCCGGGGATAACAGAT63VN
V = A, G, C; N = A, C, G, T
and block primer
                                        (SEQ ID NO. 12)
AAGCAGTGGTAACAACGCAGAGTACGCGG
``` following the protocol from Birkholz et al. (Birkholz et al, 2009).

TCR genes were amplified by PCR described by Birkholz et al. (Birkholz et al, 2009) using Advandage-Polymerase (BD, Heidelberg, Germany), 20 pmol 64T primer, and

```
20 pmol T7-capswitch primer
                                        (SEQ ID NO. 13)
TTATACGACTCACTATAGGGAGGAAGCAGTGGTAACAACGCAGAGT
(Birkholz et al, 2009).
```

The following first TCR chain-specific PCR was done with TCR-specific primers specific for the TCR α-chain with

```
40 pmol SMARTarg
                                        (SEQ ID NO. 14)
AAGCAGTGGTAACAACGCAGAGTACG
and 20 pmol Cα 3'UTR
                                        (SEQ ID NO. 15)
CTGTCTTACAATCTTGCAGATC;

or specific for the TCR β-chain with
SMARTarg, 20 pmol Cβ1 3'UTR
                                        (SEQ ID NO. 16)
CCACTTCCAGGGCTGCCTTC,
and 20 pmol Cβ2 3'UTR
                                        (SEQ ID NO. 17)
TGACCTGGGATGGTTTTGGAGCTA.
```

The amplified DNA was verified by DNA sequencing and identified via blast sequence search and alignment. The identified TCR chains were determined according to the nomenclature of Arden et al. (Arden et al. 1995) and Lefranc et al. (Lefranc et al. 2001).

The identified TCR chains were amplified by PCR using Pfunds-Polymerase (Genaxxon Bioscience GmbH, Ulm, Germany) and the following primer pairs with a concentration of 1 µg/µl:
α-chain:

AV16s1_TRAV3
(SEQ ID NO. 18)
GAC<u>TCTAGA</u>TGGCCTCTGCACCCATC
and

Calpha-XhoI
(SEQ ID NO. 19)
CT<u>CTCGAG</u>CATCTTGCAGATCTCAGCTGGACCACA;

β-chain:
BV17s1_TRBV19
(SEQ ID NO. 20)
GAC<u>TCTAGA</u>TGAGCAACCAGGTGCTCT
and

HCbeta1-XhoI/EcoRI
(SEQ ID NO. 21)
GGAATT<u>CCTCGAG</u>GGATCCCTGCCTTCAGAAATCCTTTCTC.

The PCR products were cloned into the RNA production vectors pGEMsigsurvivinDClamp (Bonehill et al, 2004) using the restriction sites XbaI and XhoI (underlined) introduced by the PCR primer (Birkholz et al, 2009). Every new construct was verified by DNA sequencing.

In-vitro transcription was performed using mMESSAGE mMACHINE® T7 Ultra Kit (Applied Biosystems/Ambion, Texas, USA) according to the manufactures' instructions. The mRNA was purified using the PureLink™ RNA Mini Kit (Invitrogen, Darmstadt, Germany) following the manufactures' protocol and the concentrations of mRNA was determined by spectrophotometrical analysis. RNA quality was verified by agarose gel electrophoresis and mRNA was stored at −80° C.

The features disclosed in the foregoing description, in the claims and/or in the accompanying drawings may, both separately and in any combination thereof, be material for realizing the invention in diverse forms thereof.

REFERENCES

Arden, B., et al., Human T-cell receptor variable gene segment families. Immunogenetics, 1995. 42(6): p. 455-500.
Berdien B, Reinhard H, Meyer S, Spöck S, Kröger N, Atanackovic D, Fehse B. Influenza virus-specific TCR-transduced T cells as a model for adoptive immunotherapy. Hum Vaccin Immunother. 2013 Feb. 21; 9(6). [Epub ahead of print]
Birkholz, K., et al., A fast and robust method to clone and functionally validate T-cell receptors. J Immunol Methods, 2009. 346(1-2): p. 45-54.
Bonehill, A., et al., Messenger RNA-electroporated dendritic cells presenting MAGE-A3 simultaneously in HLA class I and class II molecules. J Immunol, 2004. 172(11): p. 6649-57.
Boulter J M and Jakobsen B K. Stable, soluble, high-affinity, engineered T cell receptors: novel antibody-like proteins for specific targeting of peptide antigens. Clin Exp Immunol. 2005; 142(3): 454-460.
Furuse Y, Suzuki A, Kamigaki T and Oshitani H. Evolution of the M gene of the influenza A virus in different host species: large-scale sequence analysis. Virology Journal 2009, 6:67 1743-422X-6-67
Galina V. Petrova, Elena N. Naumova and Jack Gorski. The Polyclonal CD8 T Cell Response to Influenza M1 58-66 Generates a Fully Connected Network of Cross-Reactive Clonotypes to Structurally Related Peptides: A Paradigm for Memory Repertoire Coverage of Novel Epitopes or Escape Mutants. *J Immunol* 2011;
Galina V. Petrova and Jack Gorski. Cross-reactive responses to modified M158-66 peptides by CD8+ T cells that use noncanonical B V genes can describe unknown repertoires. Eur. J. Immunol. 2012. 42: 3001-3008.
Han E Q, Li X L, Wang C R, Li T F, Han S Y. Chimeric antigen receptor-engineered T cells for cancer immunotherapy: progress and challenges. *J Hematol Oncol.* 2013 Jul. 8; 6:47.
Heemskerk M H M, Hagedoorn R S, van der Hoorn M A W G, van der Veken L T, Hoogeboom M, Kester M G D, Willemze R, and Falkenburg J H F. Efficiency of T-cell receptor expression in dual-specific T cells is controlled by the intrinsic qualities of the TCR chains within the TCR-CD3 complex. Blood, 2007, VOL 109, p. 235-243.
Hofmann, C., et al., Human T cells expressing two additional receptors (TETARs) specific for HIV-1 recognize both epitopes. Blood, 2011. 118(19): p. 5174-7
Jeffrey Ishizuka, Guillaume B. E., Stewart-Jones, Anton van der Merwe, John I. Bell, Andrew J. McMichael and E. Yvonne Jones. The Structural Dynamics and Energetics of an Immunodominant T Cell Receptor Are Programmed by Its Vb Domain. Immunity 2008.
Joseph A, Zheng J H, Follenzi A, DiLorenzo T, Sango K, Hyman J, Chen K, Piechocka-Trocha A, Brander C, Hooijberg E, Vignali D A, Walker B W and Goldstein H. Lentiviral Vectors Encoding Human Immunodeficiency Virus Type 1. (HIV-1)-Specific T-Cell Receptor Genes Efficiently Convert Peripheral Blood CD8 T Lymphocytes into Cytotoxic T Lymphocytes with Potent In Vitro and In Vivo HIV-1-Specific Inhibitory Activity. Journal of Virology, March 2008, p. 3078-3089 Vol. 82, No. 6
Lefranc, M.-P., G. Lefranc, The T cell receptor FactsBook 2001. Academic Press. ISBN:0124413528 2001.
Linnemann C, Schumacher TNM and Bendle G M. T-Cell Receptor Gene Therapy: Critical Parameters for Clinical Success. Journal of Investigative Dermatology 2011, Vol. 131: 1806-1816.
Lunde E, Løset G Å, Bogen B, Sandlie I. Stabilizing mutations increase secretion of functional soluble TCR-Ig fusion proteins. BMC Biotechnology 2010, 10:61
Nakazawa Y, Huye Le E, Salsman V S, Leen A M, Ahmed N, Rollins L, Dotti G, Gottschalk S M, Wilson M H and Rooney C M. PiggyBac-mediated Cancer Immunotherapy Using EBV-specific Cytotoxic T-cells Expressing HER2-specific Chimeric Antigen Receptor. Molecular therapy 2011 December; 19(12):2133-43.
Paul J. Lehner, Eddie C. Y. Wang, Paul A. H. Moss, Sheila Williams, Kaye Platt, Steven M. Friedman, John I. Bell, and Leszek K. Borysiewicz. Human HLA-A0201-restricted Cytotoxic T Lymphocyte Recognition of Influenza A Is Dominated by T Cells Bearing the V/317 Gene Segment. J Exp Med 1995.
Porter D L, Levine B L, Kalos M, Bagg A, and June C H. Chimeric Antigen Receptor-ModifiedT Cells in Chronic Lymphoid Leukemia. N Engl J Med 2011; 365:725-33.
Shalyn C. Clute, Yuri N. Naumov, Levi B. Watkin, Nuray Asian, John L. Sullivan, David A. Thorley-Lawson, Katherine Luzuriaga, Raymond M. Welsh, Roberto Puzone, Celada F, and Selin L K., Broad cross-reactive T cell receptor repertoires recognizing dissimilar Epstein-Barr and influenza A virus epitopes. J Immunol 2010.

Verra N C V, Jorritsma A, Weijer K, Ruizendaal J J., Voordouw A, Weder P, Hooijberg E, Schumacher T N M, Haanen JBAG. Spits H, and Luiten R M. Human Telomerase Reverse Transcriptase-Transduced Human Cytotoxic T Cells Suppress the Growth of Human Melanoma in Immunodeficient Mice. Cancer Research 64, 2153-2161, Mar. 15, 2004

Widjaja L, Krauss S L, Webby R J, Xie T, and Webster R G. Matrix Gene of Influenza A Viruses Isolated from Wild Aquatic Birds: Ecology and Emergence of Influenza A Viruses Virol. 2004 August; 78(16): 8771-8779.

Zhang G, Liu R, Zhu X, Wang L, Ma J, Han H, Wang X, Zhang G, He W, Wang W, Liu C, Li S, Sun M, Gao B. Retargeting NK-92 for anti-melanoma activity by a TCR-like single-domain antibody. Immunol Cell Biol. 2013 November; 91(10):615-24. doi: 10.1038/icb.2013.45. Epub 2013 Oct. 8.

The invention claimed is:

1. A T-cell receptor comprising:
   A) a T-cell receptor α-chain, wherein said T-cell receptor α-chain comprises the amino acid sequence of LNTNAGKSTFGDGTTLTVKP (SEQ ID NO: 1) and
   B) a T-cell receptor (β-chain, wherein said T-cell receptor β-chain comprises the amino acid sequence of TSGTEAFFGQGTRLTVV (SEQ ID NO: 3),
   wherein the T-cell receptor α-chain and the T-cell receptor β-chain are linked to each other via a linker.

2. The T-cell receptor of claim 1, wherein said T-cell receptor α-chain comprises the amino acid sequence of SEQ ID NO: 2.

3. The T-cell receptor of claim 1, wherein said T-cell receptor β-chain comprises the amino acid sequence of SEQ ID NO: 4.

4. A T-cell receptor (TCR) comprising:
   (i) a T cell receptor α-chain comprising the amino acid sequence of SEQ ID NO: 1 or SEQ ID NO: 2, and
   (ii) a T-cell receptor β-chain comprising the amino acid sequence of SEQ ID NO: 3 or SEQ ID NO: 4,
   wherein the T-cell receptor α-chain and the T-cell receptor β-chain are linked to each other via a linker.

5. A soluble T-cell receptor (sTCR) construct comprising:
   (1) at least one of
      the T-cell receptor α-chain according to claim 1, and
      the T-cell receptor β-chain according to claim 1, and
   (2) at least one fusion component selected from
      Fc receptors and/or Fc domains,
      cytokines,
      toxins, and
      antibodies,
   wherein the at least one T-cell receptor chain (1) is bound to the fusion component(s) (2), and wherein the soluble T-cell receptor further comprises a label.

6. A chimeric T-cell receptor comprising at least one of:
   A) the T-cell receptor α-chain of claim 1,
   B) the T-cell receptor β-chain of claim 1 and
   C) a T-cell receptor (TCR) comprising:
      (i) a T cell receptor α-chain comprising the amino acid sequence of SEQ ID NO: 1 or SEQ ID NO: 2, and
      (ii) a T-cell receptor β-chain comprising the amino acid sequence of SEQ ID NO: 3 or SEQ ID NO: 4,
   wherein the TCR α-chain and/or the TCR β-chain is/are fused to CD3-zeta chain(s).

7. An expression construct comprising a nucleic acid encoding at least one of the following:
   I) a T-cell receptor comprising
      A) a T-cell receptor α-chain, wherein said T-cell receptor α-chain comprises the amino acid sequence of LNTNAGKSTFGDGTTLTVKP (SEQ ID NO: 1) and
      B) a T-cell receptor β-chain, wherein said T-cell receptor (β-chain comprises the amino acid sequence of TSGTEAFFGQGTRLTVV (SEQ ID NO: 3);
   II) A T-cell receptor (TCR) comprising:
      (i) a T cell receptor α-chain comprising the amino acid sequence of SEQ ID NO: 1 or SEQ ID NO: 2, and
      (ii) a T-cell receptor β-chain comprising the amino acid sequence of SEQ ID NO: 3 or SEQ ID NO: 4;
   III) A soluble T-cell receptor (sTCR) construct comprising:
      (1) at least one of
      the T-cell receptor α-chain according to claim 1, and
      the T-cell receptor β-chain according to claims 1, and
      (2) at least one fusion component selected from
         Fc receptors and/or Fc domains,
         cytokines,
         toxins, and
         antibodies,
      wherein the at least one T-cell receptor chain (1) is bound to the fusion component(s) (2), and wherein the soluble T-cell receptor further comprises a label; and IV) A chimeric T-cell receptor comprising at least one of:
   A) the T-cell receptor α-chain of claim 1,
   B) the T-cell receptor β-chain of claim 1 and
   C) a T-cell receptor (TCR) comprising:
      (i) a T cell receptor α-chain comprising the amino acid sequence of SEQ ID NO: 1 or SEQ ID NO: 2, and
      (ii) a T-cell receptor β-chain comprising the amino acid sequence of SEQ ID NO: 3 or SEQ ID NO:4,
   wherein the TCR α-chain and/or the TCR β-chain is/are fused to CD3-zeta chain(s).

8. The expression construct of claim 7, comprising:
the nucleic acid encoding the amino acid sequence of SEQ ID NO: 1 and/or SEQ ID NO: 3, or the nucleotide sequence of SEQ ID NO: 5 and/or SEQ ID NO: 7, or their complementary sequence(s) or sequence(s) that have at least 95% identity to the nucleotide sequence of SEQ ID NO: 5, and/or comprising the nucleic acid encoding the amino acid sequence of SEQ ID NO: 2 and/or SEQ ID NO: 4, the nucleotide sequence of SEQ ID NO: 6 and/or SEQ ID NO: 8, or their complementary sequence(s) or sequence(s) that have at least 95% identity to the nucleotide sequence of SEQ ID NO: 6 or SEQ ID NO: 8.

9. The expression construct of claim 7, wherein said construct further comprises promoter and terminator sequences.

10. An isolated cell comprising the expression construct of claim 7.

11. A pharmaceutical composition comprising one or more of:
I) a T-cell receptor comprising
   A) a T-cell receptor α-chain, wherein said T-cell receptor α-chain comprises the amino acid sequence of LNTNAGKSTFGDGTTLTVKP (SEQ ID NO: 1) and
   B) a T-cell receptor β-chain, wherein said T-cell receptor β-chain comprises the amino acid sequence of TSGTEAFFGQGTRLTVV (SEQ ID NO: 3),
   wherein the T-cell receptor α-chain and the T-cell receptor β-chain are linked to each other via a linker;
II) a T-cell receptor (TCR) comprising:
   (i) a T cell receptor α-chain comprising the amino acid sequence of SEQ ID NO: 1or SEQ ID NO: 2, and
   (ii) a T-cell receptor β-chain comprising the amino acid sequence of SEQ ID NO: 3 or SEQ ID NO: 4,
   wherein the T-cell receptor α-chain and the T-cell receptor β-ehain are linked to each other via a linker;
III) a soluble T-cell receptor (sTCR) construct comprising:
   (1) at least one of
   the T-cell receptor α-chain according to claim 1, and
   the T-cell receptor β-chain according to claim 1, and
   (2) at least one fusion component selected from
      Fc receptors and/or Fc domains,
      cytokines,
      toxins, and
      antibodies,
   wherein the at least one T-cell receptor chain (1) is bound to the fusion component(s) (2), and wherein the soluble T-cell receptor further comprises a label; and
IV) a chimeric T-cell receptor comprising at least one of:
   A) the T-cell receptor α-chain of claim 1,
   B) the T-cell, receptor βchain of claim 1 and
   C) a T-cell receptor (TCR) comprising:
      (i) a T cell receptor α-chain comprising the amino acid sequence of SEQ ID NO: 1 or SEQ ID NO: 2, and
      (ii) a T-cell receptor β-chain comprising the amino acid sequence of SEQ ID NO: 3 or SEQ ID NO: 4,
   wherein the TCR α-chain and/or the TCR β-chain is/are fused to CD3-zeta chain(s); and
V) an expression construct comprising a nucleic acid encoding at least one of I) through IV) above, or an isolated cell comprising said nucleic acid, and, optionally, a pharmaceutically-acceptable excipient.

* * * * *

SEQUENCE LISTING

```
<160> NUMBER OF SEQ ID NOS: 21

<210> SEQ ID NO 1
<211> LENGTH: 20
<212> TYPE: PRT
<213> ORGANISM: Homo sapiens

<400> SEQUENCE: 1

Leu Asn Thr Asn Ala Gly Lys Ser Thr Phe Gly Asp Gly Thr Thr Leu
1               5                   10                  15

Thr Val Lys Pro
            20

<210> SEQ ID NO 2
<211> LENGTH: 275
<212> TYPE: PRT
<213> ORGANISM: Homo sapiens

<400> SEQUENCE: 2

Met Ala Ser Ala Pro Ile Ser Met Leu Ala Met Leu Phe Thr Leu Ser
1               5                   10                  15

Gly Leu Arg Ala Gln Ser Val Ala Gln Pro Glu Asp Gln Val Asn Val
            20                  25                  30

Ala Glu Gly Asn Pro Leu Thr Val Lys Cys Thr Tyr Ser Val Ser Gly
        35                  40                  45

Asn Pro Tyr Leu Phe Trp Tyr Val Gln Tyr Pro Asn Arg Gly Leu Gln
    50                  55                  60

Phe Leu Leu Lys Tyr Ile Thr Gly Asp Asn Leu Val Lys Gly Ser Tyr
65                  70                  75                  80

Gly Phe Glu Ala Glu Phe Asn Lys Ser Gln Thr Ser Phe His Leu Lys
                85                  90                  95

Lys Pro Ser Ala Leu Val Ser Asp Ser Ala Leu Tyr Phe Cys Ala Val
            100                 105                 110

Arg Asp Leu Asn Thr Asn Ala Gly Lys Ser Thr Phe Gly Asp Gly Thr
        115                 120                 125

Thr Leu Thr Val Lys Pro Asn Ile Gln Asn Pro Asp Pro Ala Val Tyr
    130                 135                 140

Gln Leu Arg Asp Ser Lys Ser Ser Asp Lys Ser Val Cys Leu Phe Thr
145                 150                 155                 160

Asp Phe Asp Ser Gln Thr Asn Val Ser Gln Ser Lys Asp Ser Asp Val
                165                 170                 175

Tyr Ile Thr Asp Lys Thr Val Leu Asp Met Arg Ser Met Asp Phe Lys
            180                 185                 190

Ser Asn Ser Ala Val Ala Trp Ser Asn Lys Ser Asp Phe Ala Cys Ala
        195                 200                 205

Asn Ala Phe Asn Asn Ser Ile Ile Pro Glu Asp Thr Phe Phe Pro Ser
    210                 215                 220

Pro Glu Ser Ser Cys Asp Val Lys Leu Val Glu Lys Ser Phe Glu Thr
```

```
                225                 230                 235                 240

Asp Thr Asn Leu Asn Phe Gln Asn Leu Ser Val Ile Gly Phe Arg Ile
                245                 250                 255

Leu Leu Leu Lys Val Ala Gly Phe Asn Leu Leu Met Thr Leu Arg Leu
                260                 265                 270

Trp Ser Ser
        275

<210> SEQ ID NO 3
<211> LENGTH: 17
<212> TYPE: PRT
<213> ORGANISM: Homo sapiens

<400> SEQUENCE: 3

Thr Ser Gly Thr Glu Ala Phe Phe Gly Gln Gly Thr Arg Leu Thr Val
1               5                   10                  15

Val

<210> SEQ ID NO 4
<211> LENGTH: 308
<212> TYPE: PRT
<213> ORGANISM: Homo sapiens

<400> SEQUENCE: 4

Met Ser Asn Gln Val Leu Cys Cys Val Val Leu Cys Phe Leu Gly Ala
1               5                   10                  15

Asn Thr Val Asp Gly Gly Ile Thr Gln Ser Pro Lys Tyr Leu Phe Arg
                20                  25                  30

Lys Glu Gly Gln Asn Val Thr Leu Ser Cys Glu Gln Asn Leu Asn His
            35                  40                  45

Asp Ala Met Tyr Trp Tyr Arg Gln Asp Pro Gly Gln Gly Leu Arg Leu
        50                  55                  60

Ile Tyr Tyr Ser Gln Ile Val Asn Asp Phe Gln Lys Gly Asp Ile Ala
65                  70                  75                  80

Glu Gly Tyr Ser Val Ser Arg Glu Lys Lys Glu Ser Phe Pro Leu Thr
                85                  90                  95

Val Thr Ser Ala Gln Lys Asn Pro Thr Ala Phe Tyr Leu Cys Ala Ser
                100                 105                 110

Ser Ser Thr Ser Gly Thr Glu Ala Phe Phe Gly Gln Gly Thr Arg Leu
            115                 120                 125

Thr Val Val Glu Asp Leu Asn Lys Val Phe Pro Pro Glu Val Ala Val
        130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
                180                 185                 190

Pro Leu Lys Glu Gln Pro Ala Leu Asn Asp Ser Arg Tyr Cys Leu Ser
            195                 200                 205

Ser Arg Leu Arg Val Ser Ala Thr Phe Trp Gln Asn Pro Arg Asn His
        210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255
```

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Phe
305

<210> SEQ ID NO 5
<211> LENGTH: 60
<212> TYPE: DNA
<213> ORGANISM: Homo sapiens

<400> SEQUENCE: 5
ttaacaccaa tgcaggcaaa tcaacctttg gggatgggac tacgctcact gtgaagccaa        60

<210> SEQ ID NO 6
<211> LENGTH: 825
<212> TYPE: DNA
<213> ORGANISM: Homo sapiens

<400> SEQUENCE: 6
atggcctctg cacccatctc gatgcttgcg atgctcttca cattgagtgg gctgagagct        60
cagtcagtgg ctcagccgga agatcaggtc aacgttgctg aagggaatcc tctgactgtg       120
aaatgcacct attcagtctc tggaaaccct tatctttttt ggtatgttca atacccaac        180 cgaggcctcc agttccttct gaaatacatc acaggggata acctggttaa aggcagctat       240
ggctttgaag ctgaatttaa caagagccaa acctccttcc acctgaagaa accatctgcc       300
cttgtgagcg actccgcttt gtacttctgt gctgtgagag atcttaacac caatgcaggc       360
aaatcaacct tggggatgg gactacgctc actgtgaagc caaatatcca gaaccctgac       420
cctgccgtgt accagctgag agactctaaa tccagtgaca agtctgtctg cctattcacc       480
gattttgatt ctcaaacaaa tgtgtcacaa agtaaggatt ctgatgtgta tatcacagac       540
aaaactgtgc tagacatgag gtctatggac ttcaagagca cagtgctgt ggcctggagc       600 aacaaatctg actttgcatg tgcaaacgcc ttcaacaaca gcattattcc agaagacacc       660
ttcttcccca gcccagaaag ttcctgtgat gtcaagctgg tcgagaaaag ctttgaaaca       720
gatacgaacc taaactttca aaacctgtca gtgattgggt tccgaatcct cctcctgaaa       780
gtggccgggt taatctgct catgacgctg cggctgtggt ccagc                        825

<210> SEQ ID NO 7
<211> LENGTH: 49
<212> TYPE: DNA
<213> ORGANISM: Homo sapiens

<400> SEQUENCE: 7
atcgggcact gaagctttct ttggacaagg caccagactc acagttgta                    49

<210> SEQ ID NO 8
<211> LENGTH: 924
<212> TYPE: DNA
<213> ORGANISM: Homo sapiens

<400> SEQUENCE: 8
atgagcaacc aggtgctctg ctgtgtggtc ctttgtttcc tgggagcaaa caccgtggat        60

```
ggtggaatca ctcagtcccc aaagtacctg ttcagaaagg aaggacagaa tgtgaccctg    120
agttgtgaac agaatttgaa ccacgatgcc atgtactggt accgacagga cccagggcaa    180
gggctgagat tgatctacta ctcacagata gtaaatgact ttcagaaagg agatatagct    240
gaagggtaca gcgtctctcg ggagaagaag gaatcctttc ctctcactgt gacatcggcc    300
caaaagaacc cgacagcttt ctatctctgt gccagtagtt ctacatcggg cactgaagct    360
ttctttggac aaggcaccag actcacagtt gtagaggacc tgaacaaggt gttcccaccc    420
gaggtcgctg tgtttgagcc atcagaagca gagatctccc acacccaaaa ggccacactg    480
gtgtgcctgg ccacaggctt cttccctgac cacgtggagc tgagctggtg ggtgaatggg    540
aaggaggtgc acagtggggt cagcacagac ccgcagcccc tcaaggagca gcccgccctc    600
aatgactcca gatactgcct gagcagccgc ctgagggtct cggccacctt ctggcagaac    660
ccccgcaacc acttccgctg tcaagtccag ttctacgggc tctcggagaa tgacgagtgg    720
acccaggata gggccaaacc cgtcaccag atcgtcagcg ccgaggcctg ggtagagca    780 gactgtggct ttacctcggt gtcctaccag caagggtcc tgtctgccac catcctctat    840
gagatcctgc tagggaaggc caccctgtat gctgtgctgg tcagcgccct tgtgttgatg    900
gccatggtca agagaaagga tttc                                           924
```

```
<210> SEQ ID NO 9
<211> LENGTH: 9
<212> TYPE: PRT
<213> ORGANISM: Influenza A virus

<400> SEQUENCE: 9

Gly Ile Leu Gly Phe Val Phe Thr Leu
1               5

<210> SEQ ID NO 10
<211> LENGTH: 9
<212> TYPE: PRT
<213> ORGANISM: Human immunodeficiency virus

<400> SEQUENCE: 10

Ser Leu Tyr Asn Thr Val Ala Thr Leu
1               5

<210> SEQ ID NO 11
<211> LENGTH: 90
<212> TYPE: DNA
<213> ORGANISM: Artificial Sequence
<220> FEATURE:
<223> OTHER INFORMATION: 64T-Primer with V = A, G, C; N = A, C, G, T
<220> FEATURE:
<221> NAME/KEY: misc_feature
<222> LOCATION: (90)..(90)
<223> OTHER INFORMATION: n is a, c, g, or t

<400> SEQUENCE: 11
cgataaaagc tccggggata acagattttt tttttttttt tttttttttt tttttttttt    60
tttttttttt tttttttttt tttttttvn                                     90

<210> SEQ ID NO 12
<211> LENGTH: 29
<212> TYPE: DNA
<213> ORGANISM: Artificial Sequence
<220> FEATURE:
<223> OTHER INFORMATION: Block primer

<400> SEQUENCE: 12
```

```
aagcagtggt aacaacgcag agtacgcgg                                      29

<210> SEQ ID NO 13
<211> LENGTH: 46
<212> TYPE: DNA
<213> ORGANISM: Artificial Sequence
<220> FEATURE:
<223> OTHER INFORMATION: T7-capswitch primer

<400> SEQUENCE: 13
ttatacgact cactataggg aggaagcagt ggtaacaacg cagagt                    46

<210> SEQ ID NO 14
<211> LENGTH: 26
<212> TYPE: DNA
<213> ORGANISM: Artificial Sequence
<220> FEATURE:
<223> OTHER INFORMATION: SMARTarg primer

<400> SEQUENCE: 14
aagcagtggt aacaacgcag agtacg                                         26

<210> SEQ ID NO 15
<211> LENGTH: 22
<212> TYPE: DNA
<213> ORGANISM: Artificial Sequence
<220> FEATURE:
<223> OTHER INFORMATION: C alpha 3'UTR primer

<400> SEQUENCE: 15
ctgtcttaca atcttgcaga tc                                             22

<210> SEQ ID NO 16
<211> LENGTH: 20
<212> TYPE: DNA
<213> ORGANISM: Artificial Sequence
<220> FEATURE:
<223> OTHER INFORMATION: C beta 1 3'UTR primer

<400> SEQUENCE: 16
ccacttccag ggctgccttc                                                20

<210> SEQ ID NO 17
<211> LENGTH: 24
<212> TYPE: DNA
<213> ORGANISM: Artificial Sequence
<220> FEATURE:
<223> OTHER INFORMATION: C beta 2 3'UTR primer

<400> SEQUENCE: 17
tgacctggga tggttttgga gcta                                           24

<210> SEQ ID NO 18
<211> LENGTH: 26
<212> TYPE: DNA
<213> ORGANISM: Artificial Sequence
<220> FEATURE:
<223> OTHER INFORMATION: AV16s1_TRAV3 Primer

<400> SEQUENCE: 18
gactctagat ggcctctgca cccatc                                         26

<210> SEQ ID NO 19
<211> LENGTH: 35
<212> TYPE: DNA
```

```
<213> ORGANISM: Artificial Sequence
<220> FEATURE:
<223> OTHER INFORMATION: Calpha-XhoI primer

<400> SEQUENCE: 19
ctctcgagca tcttgcagat ctcagctgga ccaca                          35

<210> SEQ ID NO 20
<211> LENGTH: 27
<212> TYPE: DNA
<213> ORGANISM: Artificial Sequence
<220> FEATURE:
<223> OTHER INFORMATION: BV17s1_TRBV19 primer

<400> SEQUENCE: 20
gactctagat gagcaaccag gtgctct                                   27

<210> SEQ ID NO 21
<211> LENGTH: 41
<212> TYPE: DNA
<213> ORGANISM: Artificial Sequence
<220> FEATURE:
<223> OTHER INFORMATION: HCbeta1-XhoI/EcoRI  primer

<400> SEQUENCE: 21
ggaattcctc gagggatccc tgccttcaga aatcctttct c                   41
```